United States Patent
Nakano

(10) Patent No.: US 8,863,803 B2
(45) Date of Patent: Oct. 21, 2014

(54) APPARATUS FOR MANUFACTURING ABSORBENT ARTICLE

(75) Inventor: Takumi Nakano, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 13/577,939

(22) PCT Filed: Feb. 16, 2011

(86) PCT No.: PCT/JP2011/053253
§ 371 (c)(1),
(2), (4) Date: Oct. 10, 2012

(87) PCT Pub. No.: WO2011/105263
PCT Pub. Date: Sep. 1, 2011

(65) Prior Publication Data
US 2013/0020028 A1    Jan. 24, 2013

(30) Foreign Application Priority Data
Feb. 23, 2010  (JP) .................................. 2010-037847

(51) Int. Cl.
B32B 41/00    (2006.01)
(Continued)

(52) U.S. Cl.
CPC ..... *A61F 13/15772* (2013.01); *B29C 66/93451* (2013.01); *B29C 66/932* (2013.01); *B05C 5/0258* (2013.01); *B29C 65/4815* (2013.01); *B29C 66/83413* (2013.01); *B32B 2555/02* (2013.01); *B05C 11/1034* (2013.01); *B29C 65/525* (2013.01); *B32B 37/1284* (2013.01); *B05C 11/1023* (2013.01); *B29L 2031/4878* (2013.01); *B29C 66/45* (2013.01)
USPC ............. 156/378; 156/64; 156/350; 156/351; 156/353; 156/355; 156/356; 156/357; 156/362; 156/364; 156/379

(58) Field of Classification Search
CPC  B32B 2309/72; B32B 39/00; B65H 2553/42; B65H 2557/512; B65H 26/00; B65H 39/00
USPC .......... 156/64, 350, 351, 353, 355, 356, 357, 156/362, 364, 378, 379
See application file for complete search history.

(56) References Cited

U.S. PATENT DOCUMENTS 4,090,904 A * 5/1978 Mahoney ...................... 156/215
5,930,139 A * 7/1999 Chapdelaine et al. ........ 700/118
(Continued)

FOREIGN PATENT DOCUMENTS

JP    2002530130 A    9/2002
JP    2003521771 A    7/2003
(Continued)

OTHER PUBLICATIONS
International Search Report for PCT/JP2011/053253, dated Apr. 12, 2011.
(Continued)

*Primary Examiner* — Jeff Aftergut
*Assistant Examiner* — Joshel Rivera
(74) *Attorney, Agent, or Firm* — Lowe Hauptman & Ham LLP

(57) ABSTRACT

An apparatus for manufacturing an absorbent article includes: first and second reference-signal outputting sections for outputting first and second reference signals indicating a conveyance amount of a workpiece, a processing device for processing the workpiece based on a drive signal, an adhesive discharging device for discharging adhesive toward the workpiece based on a discharge signal, and a controller. While manufacturing the absorbent article, the controller generates both the drive signal and the discharge signal based on the first reference signal. While inspecting a discharge amount of the adhesive, the controller generates the discharge signal based on the second reference signal, without outputting the drive signal.

6 Claims, 10 Drawing Sheets

(51) Int. Cl.
  *B05C 5/02* (2006.01)
  *B32B 37/12* (2006.01)
  *A61F 13/15* (2006.01)
  *B29C 65/00* (2006.01)
  *B29C 65/48* (2006.01)
  *B05C 11/10* (2006.01)
  *B29C 65/52* (2006.01)
  *B29L 31/48* (2006.01)

(56) References Cited

U.S. PATENT DOCUMENTS 6,224,699 B1 5/2001 Bett et al.
7,198,690 B2 4/2007 Hoshika et al.
2003/0004594 A1 1/2003 Liu et al.
2005/0224171 A1 10/2005 Hoshika et al.

FOREIGN PATENT DOCUMENTS

JP 2005296089 A 10/2005
WO 0156523 A1 8/2001

OTHER PUBLICATIONS

Extended European Search Report dated Oct. 17, 2013, corresponds to European patent application No. 11747227.4.
Office Action dated Jan. 24, 2014, corresponds to Chinese patent application No. 201180010618.0.
Office Action mailed Sep. 24, 2013, corresponds to Japanese patent application No. 2010-037847.

* cited by examiner

CROSS SECTION ALONG LINE B-B

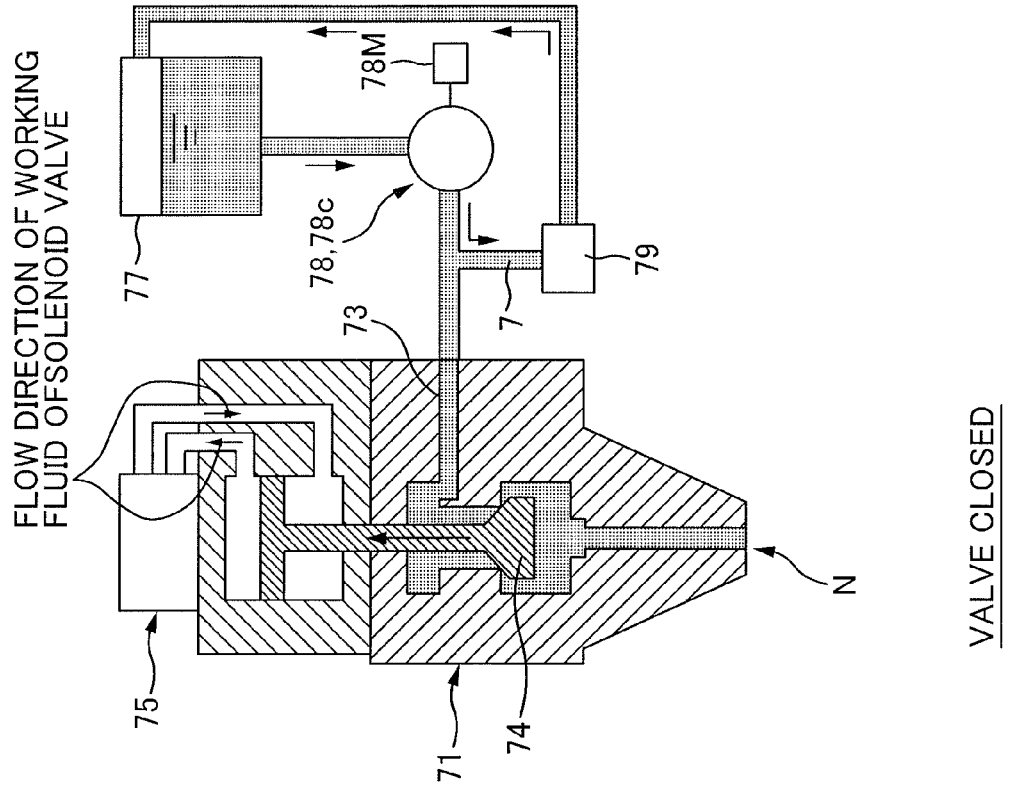
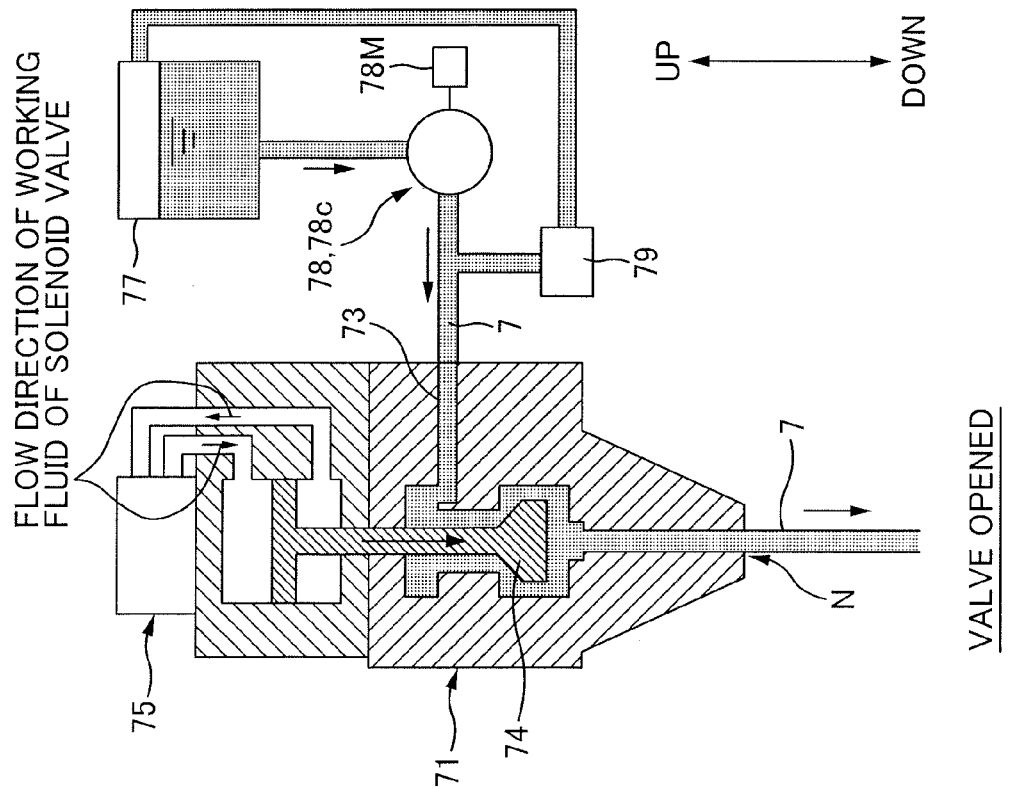

APPARATUS FOR MANUFACTURING ABSORBENT ARTICLE

RELATED APPLICATIONS

The present application is a National Phase of International Application Number PCT/JP2011/053253, filed Feb. 16, 2011, and claims priority from Japanese Application Number 2010-037847, filed Feb. 23, 2010.

TECHNICAL FIELD

The present invention relates to an apparatus for manufacturing absorbent articles such as disposable diapers.

BACKGROUND ART

Conventional manufacturing lines for manufacturing absorbent articles, such as disposable diapers, perform various processes, such as appropriate processing on a workpiece such as a nonwoven fabric, discharge of hot-melt adhesives, and adhering of other components, while conveying the workpiece in a conveying direction, to thereby fabricate the absorbent articles (see Patent Literature 1).

CITATION LIST

Patent Literature 1: JP-A-2005-296089

SUMMARY OF INVENTION

Technical Problem

The discharge of an adhesive 7 is performed by a hot-melt-adhesive discharging device 70 (referred to hereinafter as HMA discharge device 70 or HMA application device 70) (FIG. 3A). For example, the HMA discharge device 70 has a head 71 arranged at a predetermined position in the conveying direction, and the head 71 has a nozzle N. The nozzle N is provided with a valve 74 (FIGS. 4A and 4B). The valve 74 opens and closes according to the conveyance amount of a workpiece 1a under the control of a controller 80, and thereby discharges the hot-melt adhesive 7 from the nozzle N toward the workpiece 1a.

The hot-melt adhesive 7 is supplied to the head 71 by a pump 78. The amount of adhesive 7 the pump 78 supplies per unit time is increased/decreased on the basis of the conveyance speed V1 of the workpiece 1a. Thus, the adhesive 7 is applied at a predetermined basis weight (weight per unit area ($g/m^2$)), regardless of the magnitude of the conveyance speed V1 of the workpiece 1a.

In order to control the opening/closing operation of the valve 74 according to the conveyance amount, and in order to control the supply amount of the pump 78 according to the conveyance speed V1, a reference signal that is output from an encoder 45 is used. More specifically, the encoder 45 is structured so as to repeatedly output a digital value from 0 to 8191, for example, during a period in which a workpiece 1a is conveyed by a unit conveyance amount which is equivalent to a product pitch P of a diaper 1 (i.e., the length P of a single piece of product), the encoder the digital value being proportional to the conveyance amount. The controller 80 controls the opening and closing operations of the valve 74 as follows: open the valve 74 when the digital value transmitted from the encoder 45 reaches a predetermined first setting value; close the valve 74 when the digital value reaches a second setting value, and the like. The controller 80 also successively calculates the conveyance speed V1 on the basis of the time interval $\Delta T$ at which the digital values are output. On the basis of the calculated conveyance speed V1, the controller 80 performs a control to increase/decrease the supply amount of the pump 78.

Incidentally, deterioration from aging, such as the wearing of the valve 74 and/or the flow path 73 inside the head 71 and the buildup of foreign materials therein, may cause the discharge amount from the nozzle N to deviate from the target value. For this reason, the discharge amount is periodically inspected on a manufacturing line. For example, the inspection may be performed as follows. First, the encoder 45 is actuated so as to output the aforementioned reference signal, and the valve 74 and the pump 78 are operated according to a discharge pattern used at the time of actual manufacture on the basis of the reference signal. The hot-melt adhesive 7 discharged from the nozzle N at this time is received and sampled for a predetermined period of time, and the sampled amount is compared with a target discharge amount that should be discharged during the predetermined period of time. If the sampled amount is outside a permissible range with respect to the target value, then the component in question is replaced or cleaned, for example.

In general, however, the encoder 45 is provided on the driving system of a processing device 40. For example, if the processing device 40 is a pair of upper and lower pressing rolls 41 and 41, the encoder 45 is disposed of the shaft end of one of the pressing rolls 41 in an integrated manner. The encoder 45 rotates together with the pressing roll 41 when the pressing roll 41 rotates according to the conveyance of the workpiece 1a, and thus outputs the digital values of the reference signal as values indicating the conveyance amount of the workpiece 1a.

Thus, in the aforementioned construction, the processing device 40 has to be driven in order to perform the aforementioned inspection. In this case, in order to prevent the operator from getting caught in the processing device 40, sufficient safety measures such as the roping off of operation areas need to be taken; and thus, the inspection cannot be performed easily. As a result, it is difficult to increase the inspection frequency, thus inhibiting reduction in the rate of defects due to errors in the basis weight of the hot-melt adhesive 7.

The present invention has been achieved in view of such conventional problems, and an advantage thereof is to provide an absorbent-article manufacturing apparatus in which the discharge amount of a hot-melt-adhesive discharging device can be inspected safely and easily.

Solution to Problem

A principal invention for achieving the aforementioned objective is an absorbent-article manufacturing apparatus for manufacturing an absorbent article by performing processing on and discharging an adhesive onto a workpiece related to the absorbent article while conveying the workpiece in a conveying direction, the absorbent-article manufacturing apparatus including:
  a first-reference-signal outputting section that outputs a first reference signal indicating a conveyance amount of the workpiece;
  a second-reference-signal outputting section that outputs a second reference signal indicating the conveyance amount of the workpiece;
  a processing device that performs processing on the workpiece on the basis of a drive signal;

an adhesive discharging device that discharges the adhesive toward the workpiece on the basis of a discharge signal; and a controller that generates the drive signal and the discharge signal, wherein at the time of manufacturing the absorbent article, the controller generates the drive signal on the basis of the first reference signal output from the first-reference-signal outputting section and outputs the drive signal to the processing device, and the controller also generates the discharge signal on the basis of the first reference signal and outputs the discharge signal to the adhesive discharging device, and at the time of inspecting a discharge amount of the adhesive discharged from the adhesive discharging device, the controller generates the discharge signal on the basis of the second reference signal output from the second-reference-signal outputting section and outputs the discharge signal to the adhesive discharging device, and the controller does not output the drive signal to the processing device.

Other features of the present invention will be made clear through the present Description and the accompanying drawings.

Advantageous Effects of Invention

With the present invention, the discharge amount of a hot-melt-adhesive discharging device can be inspected safely and easily.

BRIEF DESCRIPTION OF DRAWINGS

FIGS. 4A and 4B are configuration diagrams of an HMA application device 70.

DESCRIPTION OF EMBODIMENTS

Figure 1:
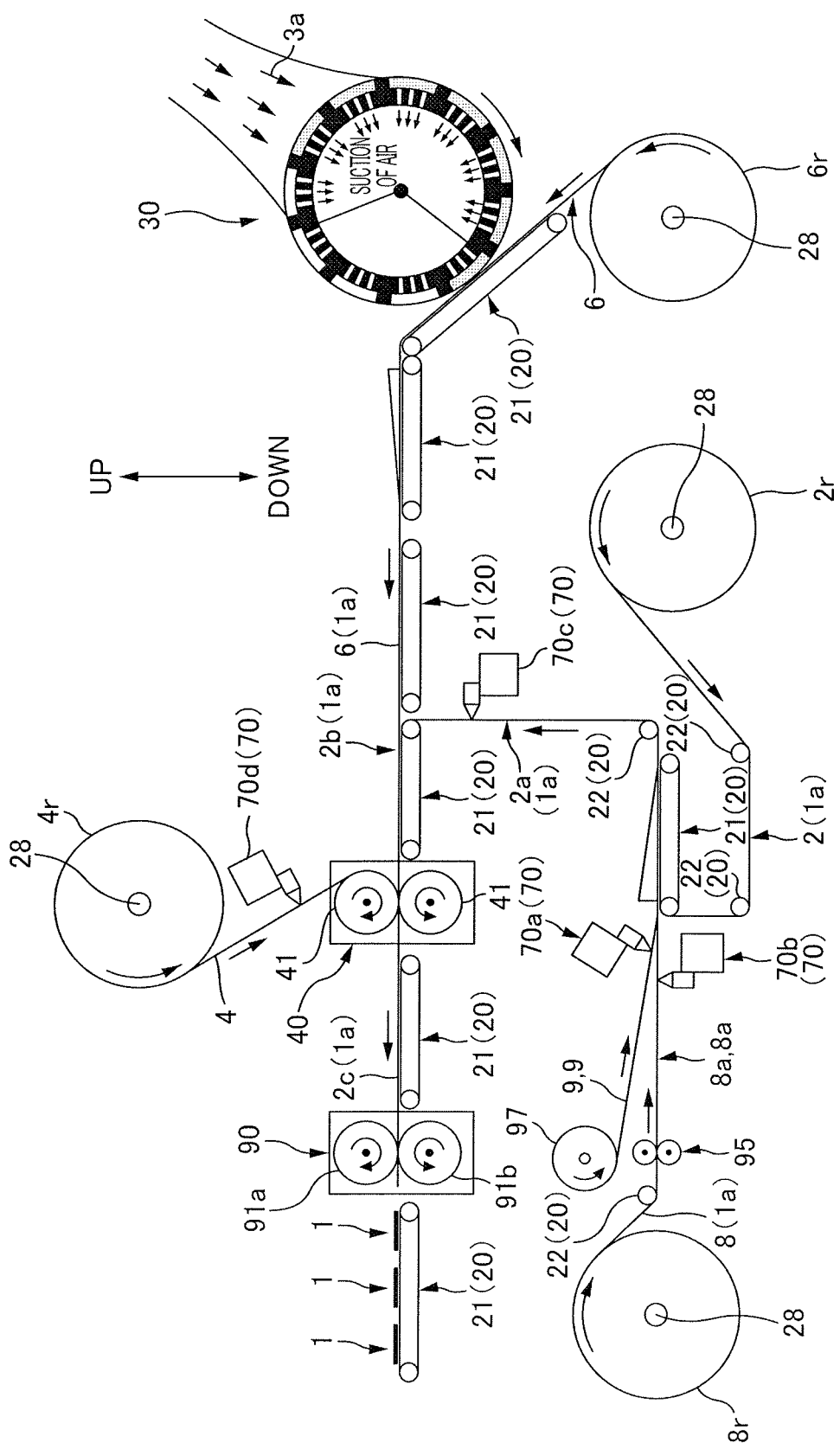
FIG. 1 is a schematic side view of a manufacturing line as an example of an apparatus for manufacturing absorbent articles.

At least the following matters will be made clear by the present Description and the accompanying drawings.

Disclosed is an absorbent-article manufacturing apparatus for manufacturing an absorbent article by performing processing on and discharging an adhesive onto a workpiece related to the absorbent article while conveying the workpiece in a conveying direction, the absorbent-article manufacturing apparatus including:

a first-reference-signal outputting section that outputs a first reference signal indicating a conveyance amount of the workpiece;

a second-reference-signal outputting section that outputs a second reference signal indicating the conveyance amount of the workpiece;

a processing device that performs processing on the workpiece on the basis of a drive signal;

an adhesive discharging device that discharges the adhesive toward the workpiece on the basis of a discharge signal; and a controller that generates the drive signal and the discharge signal, wherein at the time of manufacturing the absorbent article, the controller generates the drive signal on the basis of the first reference signal output from the first-reference-signal outputting section and outputs the drive signal to the processing device, and the controller also generates the discharge signal on the basis of the first reference signal and outputs the discharge signal to the adhesive discharging device, and at the time of inspecting a discharge amount of the adhesive discharged from the adhesive discharging device, the controller generates the discharge signal on the basis of the second reference signal output from the second-reference-signal outputting section and outputs the discharge signal to the adhesive discharging device, and the controller does not output the drive signal to the processing device.

According to this absorbent-article manufacturing apparatus, the adhesive discharging device can be operated on the basis of the second reference signal and the discharge operation performed at the time of manufacture can be simulated, even when the processing device is in a stopped state. This effectively avoids the operator from getting caught in the processing device when the operator is inspecting the adhesive discharge amount, and the inspection can be performed safely. Moreover, safety measures for the processing device can be reduced, and thus, the inspection can be performed easily. As a result, inspections can be performed more frequently.

In the aforementioned absorbent-article manufacturing apparatus, it is preferable that:

the second-reference-signal outputting section generates, as the second reference signal, a simulated signal of the first reference signal; and at the time of the inspection, the first reference signal from the first-reference-signal outputting section is stopped from being output, the simulated signal is input to the controller, and the controller generates the discharge signal on the basis of the simulated signal and outputs the discharge signal to the adhesive discharging device.

According to this absorbent-article manufacturing apparatus, the adhesive discharging device can be operated on the basis of the simulated signal of the first reference signal, and the discharge operation performed at the time of manufacture can be simulated, even when the processing device is in a stopped state during inspection. Thus, the discharge amount can be inspected safely.

Moreover, because the second-reference-signal outputting section outputs a simulated signal of the first reference signal, the discharge operation performed at the time of manufacture can be simulated with high accuracy during inspection.

In the aforementioned absorbent-article manufacturing apparatus, it is preferable that:
- the first-reference-signal outputting section includes a first rotary encoder;
- the second-reference-signal outputting section includes a second rotary encoder provided separately from the first rotary encoder;
- the second rotary encoder generates a rotation signal having the same specifications as the first reference signal by being driven and rotated by a driving source that is separate from a driving source of the first rotary encoder; and
- at the time of the inspection,
  - the first reference signal from the first rotary encoder is stopped from being output, and
  - the rotation signal of the second rotary encoder is input to the controller as the simulated signal.

According to this absorbent-article manufacturing apparatus, the adhesive discharging device can be operated on the basis of the simulated signal of the first reference signal, and the discharge operation performed at the time of manufacture can be simulated, even when the processing device is in a stopped state during inspection. Thus, the discharge amount can be inspected safely.

Moreover, because a second rotary encoder is used as the second-reference-signal outputting section and the second rotary encoder outputs a rotation signal having the same specifications as the first reference signal of the first rotary encoder, the discharge operation performed at the time of manufacture can be simulated with high accuracy during inspection.

In the aforementioned absorbent-article manufacturing apparatus, it is preferable that:
- if the conveyance amount of the workpiece equivalent to a manufacturing pitch for manufacturing the absorbent article is defined as a unit conveyance amount,
  - the first-reference-signal outputting section outputs, as the outputting of the first reference signal, a digital value having a magnitude proportional to the conveyance amount of the workpiece repeatedly for every unit conveyance amount;
- the controller includes a processor and a program executed by the processor;
- the controller has the second-reference-signal outputting section as the program; and
- the second-reference-signal outputting section finds a cumulative value by repeatedly adding up a predetermined incremental value at a predetermined cycle, and outputs the cumulative value as the second reference signal.

According to this absorbent-article manufacturing apparatus, only the adhesive discharging device is operated on the basis of the second reference signal, and the discharge operation performed at the time of manufacture can be simulated, even when the processing device is in a stopped state during inspection. Thus, the discharge amount can be inspected safely.

Moreover, because the processor of the controller generates the second reference signal by executing the program, there is no need to provide an encoder or the like, and thus, the number of devices can be reduced.

In the aforementioned absorbent-article manufacturing apparatus, it is preferable that:
- the first-reference-signal outputting section also serves as the second-reference-signal outputting section;
- if the processing device is defined as a first processing device,
  - the manufacturing apparatus includes a second processing device in addition to the first processing device;
- at the time of manufacturing the absorbent article,
  - the first-reference-signal outputting section outputs the first reference signal on the basis of a driving operation of the second processing device; and
- at the time of inspecting the discharge amount of the adhesive discharged from the adhesive discharging device,
  - the controller drives the second processing device, and thus, the first-reference-signal outputting section outputs the first reference signal as the second reference signal.

According to this absorbent-article manufacturing apparatus, the first-reference-signal outputting section also serves as the second-reference-signal outputting section, and thus, the number of devices can be reduced. Moreover, because the drive signal is stopped from being output to the first processing device during inspection, safety regarding the first processing device can be ensured easily and reliably.

In the aforementioned absorbent-article manufacturing apparatus, it is preferable that:
- the first-reference-signal outputting section includes a rotary encoder;
- the first-reference-signal outputting section outputs the first reference signal by being driven and rotated by a driving source provided separately from a driving source of the processing device;
- the first-reference-signal outputting section also serves as the second-reference-signal outputting section;
- at the time of manufacturing the absorbent article,
  - the controller generates the drive signal on the basis of the first reference signal and outputs the drive signal to the driving source of the processing device; and
- at the time of the inspection,
  - the controller stops outputting the drive signal to the driving source of the processing device,
  - the controller generates the discharge signal on the basis of the first reference signal by employing the first reference signal output from the first-reference-signal outputting section as the second reference signal, and
  - the controller outputs the discharge signal to the adhesive discharging device.

According to this absorbent-article manufacturing apparatus, the adhesive discharging device can be operated on the basis of the first reference signal, and the discharge operation performed at the time of manufacture can be simulated, even when the processing device is in a stopped state during inspection. Thus, the discharge amount can be inspected safely.

Moreover, because the first reference signal used at the time of manufacture can also be used during inspection, the discharge operation performed at the time of manufacture can be replicated reliably even during inspection.

The aforementioned absorbent-article manufacturing apparatus is characterized in that:
- the adhesive discharging device includes
  - a head that has at least one discharge opening,
  - a pump that supplies the adhesive to the discharge opening of the head, and
  - a valve that is provided in correspondence with the discharge opening and that intermittently discharges the adhesive from the discharge opening by performing an opening/closing operation; and the discharge signal includes
- a supply amount signal that defines a supply amount of the adhesive supplied from the pump to the head per unit time, and
- a valve open/close signal that defines the opening/closing operation of the valve.

According to this absorbent-article manufacturing apparatus, controlling the opening/closing operation of the valve enables the adhesive not only to be continuously discharged but also to be intermittently discharged. Moreover, by controlling the supply amount from the pump, the basis weight of the adhesive can be kept constant regardless of the conveyance speed of the workpiece, and also, the basis weight can be changed partially.

In the aforementioned absorbent-article manufacturing apparatus, it is preferable that:
- the workpiece is conveyed in the conveying direction by a conveyance mechanism;
- the conveyance mechanism is driven on the basis of the drive signal output from the controller;
- at the time of manufacturing the absorbent article, the controller generates the drive signal and outputs the drive signal to the conveyance mechanism; and
- at the time of inspecting the discharge amount of the adhesive discharged from the adhesive discharging device, the controller stops outputting the drive signal to the conveyance mechanism.

According to this absorbent-article manufacturing apparatus, the workpiece conveyance mechanism is also stopped during inspection. This effectively avoids the operator from getting caught in the conveyance mechanism when the operator is inspecting the adhesive discharge amount, and the inspection can be performed even more safely.

In the aforementioned absorbent-article manufacturing apparatus, it is preferable that:
- a plurality of the adhesive discharging devices are arranged at respective positions along the conveying direction; and
- at the time of inspecting the discharge amount of the adhesive discharged from each adhesive discharging device,
  - the controller generates, on the basis of the second reference signal output from the second-reference-signal outputting section, a plurality of the discharge signals in correspondence with the respective adhesive discharging devices, and
  - the controller outputs each of the generated discharge signals to a corresponding one of the adhesive discharging devices.

According to this absorbent-article manufacturing apparatus, the discharge amount inspection can be performed at the same time for a plurality of adhesive discharging devices, and the inspection time can be shortened.

—First Embodiment—

FIG. 1 is a schematic side view of a manufacturing line as an example of an apparatus for manufacturing absorbent articles. This manufacturing line manufactures disposable diapers 1 as an example of absorbent articles that absorb excreted fluids.

Figure 2A:
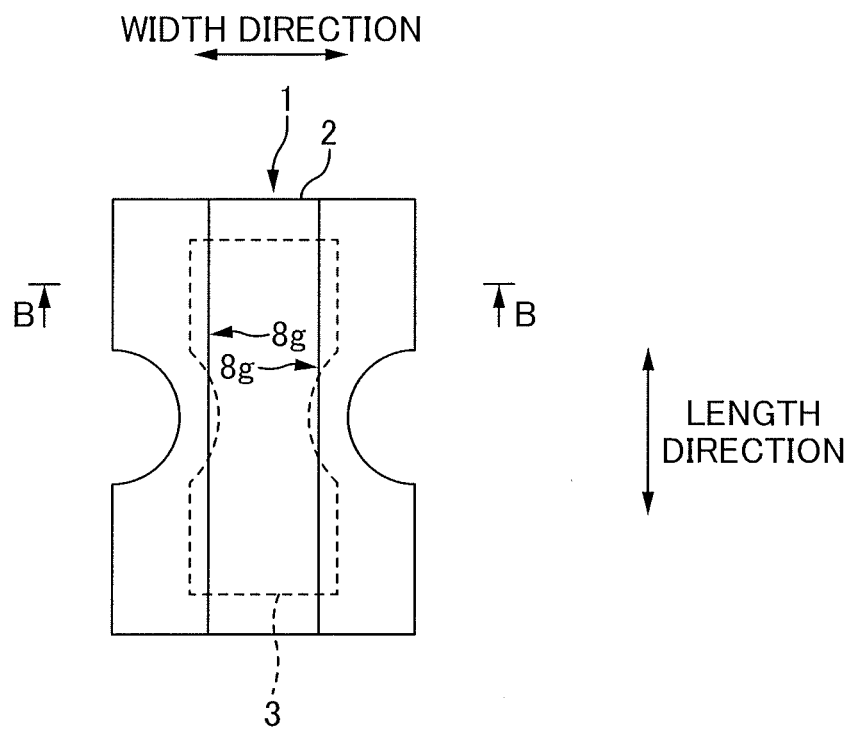
FIG. 2A is a schematic plan view of a diaper 1.
Figure 2B:
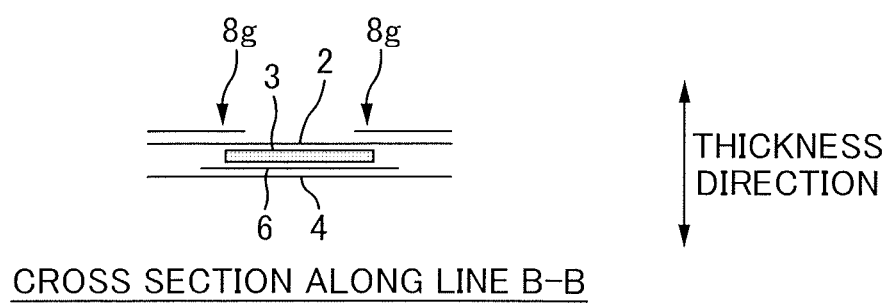
FIG. 2B is a cross-sectional view taken along line B-B in FIG. 2A.

FIG. 2A is a schematic plan view of a diaper 1, and FIG. 2B is a cross-sectional view taken along line B-B in FIG. 2A. For example, the diaper 1 has a main body including: a top sheet 2 made of e.g. a nonwoven fabric; a back sheet 4 made of e.g. a film; an absorber 3 made of e.g. pieces of pulp fiber; and a carrier sheet 6 made of e.g. tissue paper, the absorber 3 and the carrier sheet 6 being placed between the top sheet 2 and the back sheet 4. The diaper 1 also includes a pair of three-dimensional gathers 8g and 8g provided on the top sheet 2 at respective left and right sections thereof in the width direction of the diaper 1.

As illustrated in FIG. 1, the manufacturing line of the diapers 1 includes a plurality of conveyance mechanisms 20, 20, . . . that convey the semi-finished products of the diapers 1 (corresponding to "workpieces") in the conveying direction. These conveyance mechanisms 20 employ belt conveyors 21 having an adsorptive function on the surface where the workpieces are placed as well as conveyance rollers 22, the belt conveyors and conveyance rollers being driven by respective motors (not illustrated) serving as driving sources. While the semi-finished products 1a are conveyed in the conveying direction by the conveyance mechanisms 20, 20, . . . , the semi-finished products 1a are sequentially subjected to various processes including: various types of processing such as pressing, blanking, etc.; application (also referred to hereinafter as "discharge") of hot-melt adhesives; and adhering of other semi-finished products 1a serving as components. Thus, diapers 1 are fabricated.

Note that the term "semi-finished product 1a" as used herein refers to any component in any state until it is made into a diaper 1 in its finished form. For example, a semi-finished product 1a may refer to a top sheet 2 paid out from a top sheet roll 2r (described further below) or to a top sheet 2a to which three-dimensional gather sheets 8a have been bonded.

Hereinbelow, the conveying direction is also referred to as "MD direction", and the direction that is orthogonal to the MD direction but is not the thickness direction of the semi-finished product 1a (i.e., the width direction of the sheet in cases where the semi-finished product 1a is a continuous sheet) is also referred to as "CD direction".

As illustrated in FIG. 1, the manufacturing line includes a plurality of reels 28, 28, . . . . For example, a reel 28 is prepared for each of the top sheet 2, the back sheet 4, the carrier sheet 6, and the gather sheet 8. These sheets 2, 4, 6, and 8 are carried into the manufacturing line in the form of sheet rolls prepared by rolling up the respective sheets. The sheet rolls 2r, 4r, 6r, and 8r are attached to their respective, corresponding reels 28 and are paid out in the form of continuous sheets.

The manufacturing line includes, as principal processing devices, a fiber-depositing device 30, a pressing-roll device 40, a die cutter device 90, and the like, and also includes HMA application devices 70, 70, . . . (corresponding to "adhesive discharging devices") at a plurality of locations in the conveying direction.

The fiber-depositing device 30 produces absorbers 3 (not illustrated in FIG. 1) by shaping pieces of pulp fibers 3a into a predetermined shape, such as a substantially rectangular parallelepiped. And, the fiber-depositing device 30 places the produced absorbers 3 on the carrier sheet 6 at product pitches P in the conveying direction. The pressing-roll device 40 presses the semi-finished product 1a with a pair of upper and lower pressing rolls 41 and 41 when the semi-finished product 1a passes through the nip between the pressing rolls 41 and 41. This will be described further below. The die cutter device 90 includes a cutter roll 91a and an anvil roll 91b that oppose one another. The die cutter device 90 cuts the semi-finished product 1a into the outer shape of the diaper 1 when the semi-finished product 1a passes through the nip between these rolls. Note that these rolls 41, 91a, and 91b rotate about their respective rotation axes pointing in the CD direction. And, these rolls 41, 91a, and 91b are driven and rotates by acquiring rotational force from respective motors so that the semi-finished product 1a is conveyed in the conveying direction. Before different types of semi-finished products 1a and 1a are merged together, the HMA application device 70 discharges a hot-melt adhesive 7 toward either one of the semi-finished products 1a and 1a, and the semi-finished products 1a and 1a adhere to each other with the adhesive. This will also be described further below.

With the manufacturing line constructed as mentioned above, the diapers 1 are manufactured as follows, for example.

First, the gather sheet 8 is paid out from the gather sheet roll 8r and is conveyed in the MD direction by the conveyance mechanisms 20. While being conveyed, the gather sheet is split by a slitter device 95 into two narrow strips at the center of the CD direction, thus being formed into a pair of three-dimensional gather sheets 8a and 8a.

The pair of three-dimensional gather sheets 8a and 8a are conveyed in parallel to one another. While being conveyed, the pair of sheets are supplied with stretched elastic members 9 and 9, such as rubber threads, from an elastic-member supplying device 97. To each elastic member 9 and 9, an adhesive is applied in advance by a first HMA application device 70a. Thus, with the adhesive, the stretched elastic members 9 and 9 each adhere to the corresponding three-dimensional gather sheets 8a and 8a. Therefore, the three-dimensional gather sheets 8a and 8a are provided with an elastic force which is necessary when forming the three-dimensional gathers 8g and 8g.

On the other hand, an adhesive is applied by a second HMA application device 70b onto the opposite surface of each three-dimensional gather sheet 8a and 8a to the surface to which the elastic members 9 have adhered. Onto this surface, the top sheet 2 paid out from the top sheet roll 2r is placed and bonded while being conveyed in the MD direction. Therefore, a top sheet 2a having the three-dimensional gathers 8g and 8b is formed.

An adhesive is also applied by a third HMA application device 70c onto the opposite surface of the top sheet 2a to the surface provided with the three-dimensional gathers 8g. Onto this surface, the carrier sheet 6 paid out from the carrier sheet roll 6r is placed and bonded while being conveyed in the MD direction.

Note here that the carrier sheet 6 has passed the position of the fiber-depositing device 30 before being bonded as above. Thus, the opposite surface of the carrier sheet 6 to the surface which is to be bonded with the top sheet 2a already has a plurality of absorbers 3 (not illustrated in FIG. 1) placed thereon at product pitches P in the MD direction.

Next, the top sheet 2b to which the carrier sheet 6 has been bonded is conveyed in the MD direction and reaches the merging point with the back sheet 4. More specifically, the back sheet 4 paid out from the back sheet roll 4r is conveyed in the MD direction on this merging point. An adhesive is applied to the back sheet 4 by a fourth HMA application device 70d in advance before the back sheet reaches the merging point. Thus, at the merging point, the back sheet 4 is bonded to the top sheet 2b so as to cover the absorbers 3 on the carrier sheet 6.

Note that the pressing-roll device 40 is located at this merging point. Thus, almost at the same time as the bonding of the top sheet 2b and the back sheet 4, the sheets 2b and 4 are pressed by the pressing rolls 41 and 41 and adhere to each other firmly.

Then, the top sheet 2c to which the back sheet 4 has been bonded is conveyed along the MD direction to the die cutter device 90, and the die cutter device 90 separates the sheet into the outer shapes of disposable diapers 1. The disposable diapers 1 are fabricated as described above.

Figure 3A:
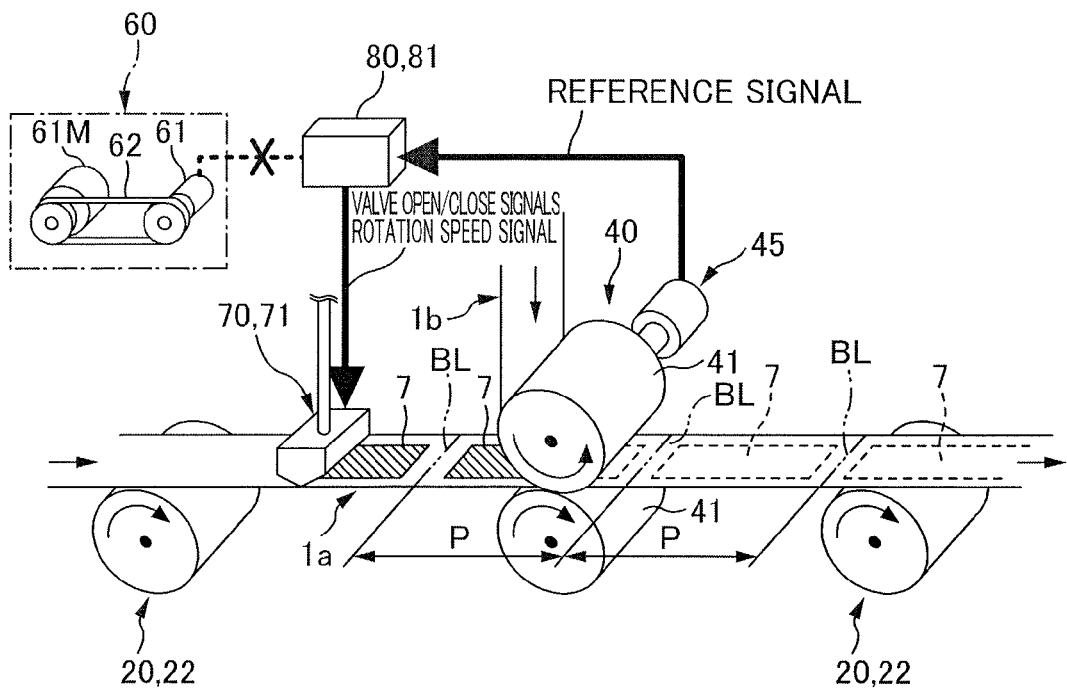
FIGS. 3A and 3B are schematic perspective views illustrating, in a generalized manner, the device constructions in a manufacturing line according to a first embodiment for clearly explaining the concept of the present invention.
Figure 3B:
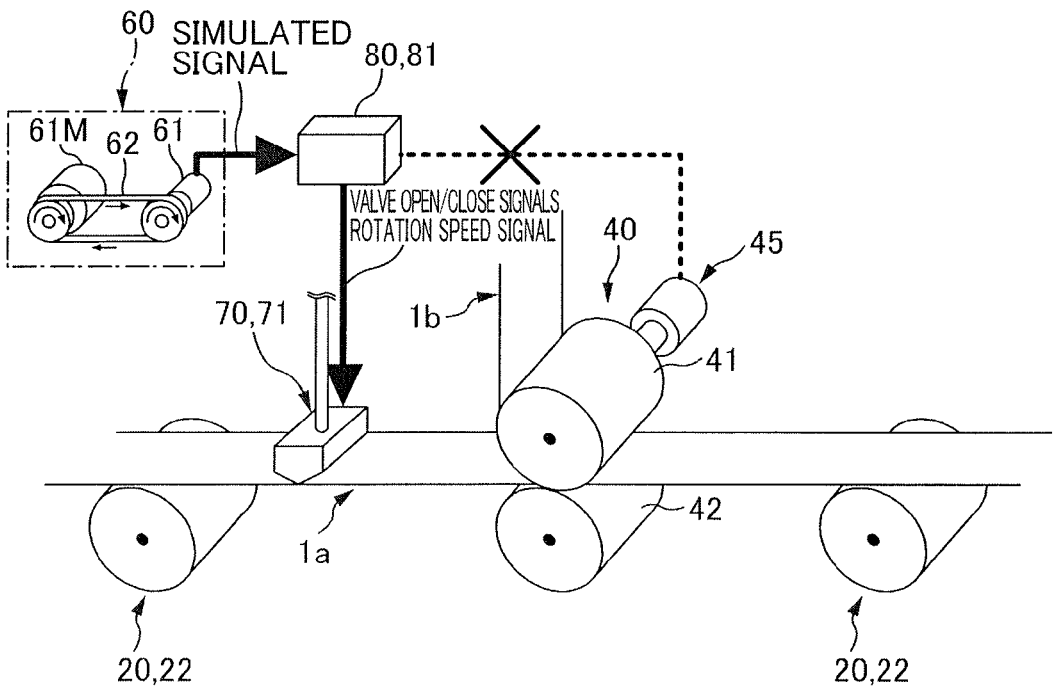

FIGS. 3A and 3B are schematic perspective views illustrating the generalized device constructions in the aforementioned manufacturing line, for clearly explaining the concept of the present invention. Note that FIG. 3A illustrates the state where the diapers 1 are manufactured, and FIG. 3B illustrates a state where the discharging amount of the HMA application device 70 is inspected.

As illustrated in FIG. 3A, the aforementioned manufacturing line can be generalized (modeled) as a construction including: the conveyance mechanisms 20; the processing device 40; the HMA application device 70; and a controller 80 that controls these devices. In the description below, the aforementioned construction performs the following processes.

First, while a first sheet 1a (corresponding to "workpiece"), which is a semi-finished product, is being conveyed in the MD direction by the conveyance mechanisms 20, the HMA application device 70 applies an adhesive 7 onto the first sheet 1a. Downstream thereof, the first sheet 1a passes through the nip between the rolls of the pressing-roll device 40, which serves as a processing device. At this time, a second sheet 1b, which is also a semi-finished product, is supplied toward the nip between the rolls. The second sheet 1b is placed on the first sheet 1a, and the sheets are pressed by the pressing-roll device 40. In this way, the first sheet 1a and the second sheet 1b are joined with the adhesive 7.

As illustrated in FIG. 3A, on the first sheet 1a, a layout of a plurality of diapers 1 lined up in the MD direction at the product pitch P is planned. In other words, target positions where various components will be joined or processed are planned. For example, the HMA application device 70 intermittently applies the adhesive 7 to a given predetermined range in the diaper 1, the range being a target application range for the adhesive 7 (the hatched range in FIG. 3A). In this example, identification of which of target processing positions in the diaper 1 corresponds to the portion that is currently being processed by the processing device is performed with reference to the pressing-roll device 40. This will be described further below.

The components 20, 40, 70, and 80 in the manufacturing line according to the present invention are described below with reference to FIG. 3A.

Conveyance Mechanism 20:

Each conveyance mechanism 20 includes: a conveyance roller 22; and a motor 22M (FIG. 5) as a driving source for driving and rotating the conveyance roller 22, for example. The first sheet 1a is conveyed in the MD direction at a predetermined conveyance speed V1 by the driving/rotation of the conveyance roller 22.

Pressing-Roll Device 40:

The pressing-roll device 40 includes a pair of upper and lower pressing rolls 41 and 41 which are driven and rotated by a motor 41M (FIG. 5) serving as a driving source. The perimeter of each pressing roll 41 is set to the same value as the length of the product pitch P of the diaper 1. Thus, when the pressing rolls 41 make one revolution, the first sheet 1a is conveyed in the MD direction by the length P (m) corresponding to a single piece of product. Hereinbelow, the conveyance amount corresponding to this product pitch P is also referred to as "unit conveyance amount".

It should be noted that a rotary encoder 45 is provided on the shaft end of the pressing roll 41. A portion of the encoder 45 rotates integrally with the pressing roll 41. On the basis of the input due to this rotational operation, the encoder 45 outputs, for every unit conveyance amount, 8192 digital values (corresponding to "value indicating the conveyance amount") ranging, e.g., from 0 to 8191 proportionately to the conveyance amount.

The digital values are set such that the value "0 (zero)" corresponds to the boundary position BL between products adjacent to one another in the MD direction. More specifically, when the boundary position BL passes through the nip between the pressing rolls 41, the encoder 45 outputs the digital value "0", and then, the encoder sequentially outputs digital values ranging from "1" to "8191" until the passage of the next boundary position BL. So, according to these digital values, it is possible to detect in real time which section of the diaper 1 is currently passing the pressing rolls 41 and 41 and which section is being pressed thereby. That is, identification which of target positions in a diaper 1 corresponds to the section that is currently being processed can be performed with reference to the pressing-roll device 40.

Thus, the digital values are transmitted to the controller 80 as a reference signal, for example, and is used, e.g., for controlling the operation of the HMA application device 70 of discharging the adhesive 7. Note that, hereinbelow, the digital values are referred to also as a "reference signal", and the encoder 45 outputting the reference signal is referred to also as a "reference encoder 45" in distinction from other encoders. The reference encoder 45 corresponds to the "first-reference-signal outputting section", and the reference signal corresponds to the "first reference signal".

HMA Application Device 70:
FIGS. 4A and 4B are configuration diagrams of the HMA application device 70. Both figures illustrate a vertical cross-section of the head 71.

The HMA application device 70 includes a head 71, a tank 77 for storing the adhesive 7, and a pump 78 for sending the adhesive 7 in the tank 77 under pressure to the head 71.

The head 71 has, for example, one long slit-shaped nozzle N (corresponding to "discharge opening") along the CD direction, and a flow path 73 for the adhesive 7. The flow path 73 is in communication with the slit-shaped nozzle N. A valve 74 for opening and closing the flow path 73 is provided in the flow path 73, and a solenoid valve 75 is provided on the valve 74. Thus, by sending a valve open/close signal (corresponding to "discharge signal") from the controller 80 to the solenoid valve 75, the valve 74 is opened and closed by the solenoid valve 75, and thus, the hot-melt adhesive 7 is discharged intermittently from the nozzle N toward the first sheet 1a. Thus, as illustrated in FIG. 3A, the adhesive 7 is discharged onto each target application region which is defined on the first sheet 1a at the product pitch P of the diaper 1.

Although this example illustrates a construction in which the head 71 has only one slit-shaped nozzle N for the sake of convenience of explanation, the construction is not limited thereto. For example, the head 71 may include a plurality of nozzles lined up in the CD direction; the flow path may be branched to form branched paths for each nozzle inside the head 71; and a valve 74 for opening/closing each flow path may be provided for each branched path. In this case, a solenoid valve 75 will be provided for each valve 74. And, each valve 74 will be opened and closed by the corresponding solenoid valve 75 by sending a valve open/close signal from the later-described controller 80 to each solenoid valve 75.

The pump 78 is a pump whose discharge rate (supply rate to the head 71) can be changed, and is a gear pump, for example. More specifically, the pump 78 includes: a casing 78C that forms the outer shape of the pump 78; a gear (not illustrated) that is provided inside the casing 78C and that is for sending the adhesive; and a motor 78M serving as a driving source that drives and rotates the gear. By increasing/decreasing the rotation speed of the gear, it is possible to increase/decrease the supply rate (cc/min) of adhesive 7, which is the supply amount thereof per unit time. Basically, the rotation speed of the gear is increased/decreased and changed on the basis of the conveyance speed V1 of the first sheet 1a. Thus, the adhesive 7 is applied at a predetermined basis weight (weight per unit area $(g/m^2)$), regardless of the magnitude of the conveyance speed V1 of the first sheet 1a. This will also be described in the explanation of the controller 80.

Incidentally, when the valve 74 is closed as illustrated in FIG. 4B, if the gear is rotated according to the conveyance speed V1 of the first sheet 1a, the adhesive 7 that is sent from the pump 78 under pressure will be sealed inside the head 71 and the pressure of the adhesive 7 becomes high. This is dangerous because the motor 78M of the pump 78 will be overloaded. So, in order to prevent this, a relief valve 79 is provided in the flow path between the pump 78 and the valve 74. The relief valve 79 is structured so as to open when the pressure inside the flow path 73 exceeds a first predetermined value. And thereby, the adhesive 7 returns to the tank 77. It should be noted that the relief valve 79 is structured so as to close when the pressure falls below a second predetermined value smaller than the first predetermined value.

Figure 5:
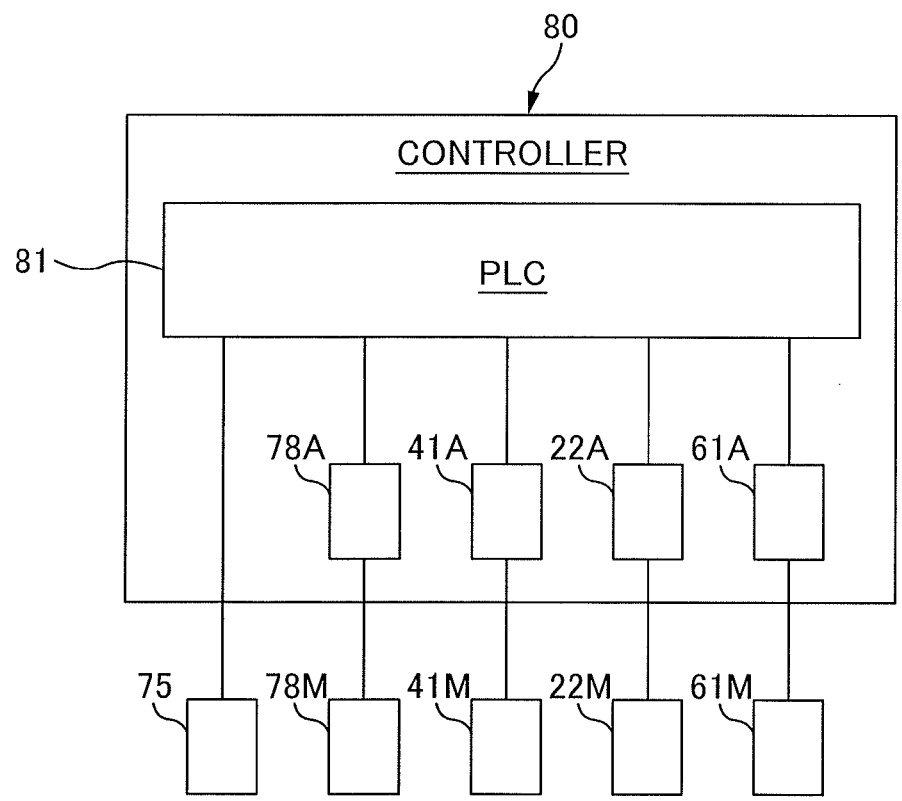
FIG. 5 is a schematic configuration diagram of a controller 80 according to the first embodiment.

Controller 80:
FIG. 5 is a schematic configuration diagram of the controller 80.

The controller 80 includes: a programmable logic controller (PLC) 81; and amplifiers 78A, 41A, 22A, and 61A provided for the motors 78M, 41M, 22M, and 61M, respectively.

The PLC 81 includes a processor. The processor executes a program stored in advance in the PLC 81, and thus, the PLC outputs various control signals to the various devices.

For example, the PLC outputs a valve open/close signal (corresponding to "discharge signal") to the solenoid valve 75 of the HMA application device 70. And the PLC outputs a signal of a command value indicating the rotation speed (rpm) of the gear (corresponding to "supply amount signal" and "discharge signal") to the amplifier 78A of the motor 78M of the pump 78. The PLC also outputs a signal of a command value indicating the rotation speed (rpm) of the pressing rolls 41 to the amplifier 41A of the motor 41M of the pressing rolls 41. And the PLC outputs a signal of a command value indicating the rotation speed (rpm) of the conveyance roller 22 to the amplifier 22A of the motor 22M of the conveyance roller 22.

The amplifiers 78A, 41A, and 22A are provided corresponding to the motors 78M, 41M, and 22M, respectively. Based on the respective rotation-speed command-value signals transmitted from the PLC 81, the amplifiers output drive signals to the corresponding motors 78M, 41M, and 22M so as to reduce the deviation between the command value and the actual value of the rotation speed. An example of this control method is the so-called PID control (proportional-integral-derivative control). In the present example, the aforementioned drive signals are also drive currents; that is, the motors 78M, 41M, and 22M are driven by employing these drive currents as their motive force.

Note here that the actual value of the rotation speed (rpm) is measured by an encoder provided on each motor 78M, 41M, 22M and is transmitted to the corresponding amplifier 78A, 41A, 22A as an actual-value signal. As for the pressing-roll device 40 which serves as the processing device, this encoder is the aforementioned reference encoder 45 outputting the reference signal. More specifically, the actual value of the rotation speed (rpm) is calculated based on the time interval ΔT; according to this time interval ΔT, the digital values in the reference signal are output. Accordingly, in the pressing roll 41 serving as the processing device, the drive signal is generated on the basis of the reference signal.

It should be noted that the motor 61M and the amplifier 61A in FIG. 5 are features related to the simulated-signal outputting section 60 illustrated in FIG. 3, which will be described further below.

At the time of manufacturing the diapers 1, the thus-constructed controller 80 operates the HMA application device 70 and the pressing-roll device 40 according to the conveyance operation of the first sheet 1a, as described below.

First, in a memory in the PLC 81 of the controller 80, a first setting value and a second setting value are stored in advance corresponding to the target application region in the diaper 1; the first setting value indicates the timing for opening the valve 74 and the second setting value indicates the timing for closing same. When the digital value of the reference signal input from the reference encoder 45 reaches the first setting value, the PLC 81 transmits a valve open signal to the solenoid valve 75, and when the digital value reaches the second setting value which is larger than the first setting value, the PLC 81 transmits a valve close signal to the solenoid valve 75, thus performing the opening/closing operation of the valve 74. More specifically, the PLC 81 performs a comparison computation as to whether the digital value has exceeded the first setting value or the second setting value at a predetermined control cycle Tc of 1 millisecond, for example. A valve close signal is output in cases where the result of the comparison computation is not greater than the first setting value; a valve open signal is output in cases where the result is greater than the first setting value but not greater than the second setting value; and a valve close signal is output in cases where the result is greater than the second setting value.

Note here that, as described above, the reference encoder 45 repeatedly outputs digital values ranging from "0" to "8191" during a period in which the first sheet 1a is conveyed by a unit conveyance amount. Accordingly, the opening/closing operation of the valve 74 is performed at every unit conveyance amount. Thus, the adhesive 7 is discharged intermittently toward each target application region defined on the first sheet 1a at every product pitch P of the diaper 1.

Moreover, as for the pump 78, the PLC 81 changes the rate at which the adhesive 7 is supplied by the pump 78; the rate is substantially proportional to the conveyance speed V1 of the first sheet 1a. More specifically, the PLC 81 first executes operations according to Equation (1) below, thereby the conveyance speed V1 is calculated based on the time interval ΔT at which the digital values in the reference signal are output.

$$V1 = \Delta D / \Delta T \quad (1)$$

The ΔD in Equation (1) refers to an increment ΔD of the conveyance amount of the first sheet 1a from the time of output of a predetermined digital value (e.g., 8190) to the time of output of the next digital value (e.g., 8191). It should be noted that ΔD is a known value unique to the reference encoder 45.

The PLC 81 performs the calculation of Equation (1) repeatedly at the control cycle Tc and thereby finds the conveyance speed V1 in real time. Then, the PLC changes in real time the command value indicating the rotation speed (rpm) of the gear of the pump 78 and successively transmits a signal of the command value to the amplifier 78A of the motor 78M of the pump 78; the rotation speed is proportional to the amount of change in the conveyance speed V1 from a predetermined reference speed Vb. Thus, the supply rate of the adhesive 7 is changed according to the conveyance speed V1 of the first sheet 1a, and the adhesive 7 is applied on the first sheet 1a at a substantially constant basis weight, regardless of the magnitude of the conveyance speed V1 of the first sheet 1a.

On the other hand, to the amplifier 22A of the motor 22M driving the conveyance rollers 22, the PLC 81 transmits a signal of the command value of the rotation speed (rpm). The command value of the rotation speed (rpm) is calculated by dividing the command value of the conveyance speed V1 (m/min) of the first sheet 1a by the perimeter (m) of the conveyance roller 22. The PLC 81 performs this division calculation at the aforementioned control cycle Tc and transmits the result thereof to the amplifier 22A every time. To the amplifier 41A of the motor 41M driving the pressing rolls 41, the PLC 81 also transmits a signal of the command value of the rotation speed (rpm). Likewise, the command value of the rotation speed (rpm) is calculated by dividing the command value of the conveyance speed V1 (m/min) of the first sheet 1a by the perimeter (m) of the pressing roll 41, and the PLC 81 performs this division calculation at the control cycle Tc and transmits the result thereof to the amplifier 41A every time. Thus, the peripheral speed (m/min) of each pressing roll 41 is controlled so as to be substantially the same as the peripheral speed (m/min) of each conveyance roller 22. As a result, the pressing rolls 41 are rotated in synchronization (in cooperation) with the conveyance operation of the first sheet 1a.

Incidentally, as for the command value of the conveyance speed V1 of the first sheet 1a that is used for calculating the command value of the rotation speed of the conveyance roller 22, the calculation may be based on the digital values in the reference signal of the reference encoder 45 of the pressing roll 41. In other words, the conveyance speed V1, which is found according to the aforementioned Equation (1) and the reference signal, may be used as the command value of the conveyance speed V1 for the conveyance rollers 22. In this way, the synchronization between the conveyance operation of the pressing rolls 41 and the conveyance operation of the conveyance rollers 22 can be further improved.

Inspection of Discharge Amount of HMA Application Device 70:

As described above, in the manufacturing line, the discharge amount of the HMA application device 70 is inspected periodically. This inspection is performed as follows. First, the HMA application device 70 is actuated as illustrated in FIG. 3A to replicate the discharge state during manufacture. Then, an inspection operator places a plate material (not illustrated) in opposition to the nozzle N of the head 71; with the plate material, the inspection operator receives and samples the adhesive 7 discharged from the nozzle N for a predetermined period of time. The sampled amount is compared with a target discharge amount that should be discharged during the predetermined period of time. If the sampled amount is within a permissible range, then it is determined that there is no problem. On the other hand, if the sampled amount is outside the permissible range, then it is determined that there is a problem, and the component considered to be problematic in the HMA application device 70 is replaced or cleaned, for example.

As described above, the PLC 81 controls the discharge operation of the HMA application device 70 on the basis of the reference signal. Thus, at the time of the aforementioned inspection, unless the pressing-roll device 40 serving as the processing device is driven as illustrated in FIG. 3A, the reference signal cannot be transmitted from the reference encoder 45 to the PLC 81, and thus, the HMA application device 70 cannot be actuated. However, if the pressing-roll device 40 is driven, the inspection operator may get caught in the pressing rolls 41, which is not preferable for safety reasons.

So, in the present first embodiment, a simulated-signal outputting section 60 (corresponding to "second-reference-signal outputting section") that generates and outputs a simulated signal (corresponding to "second reference signal") of the reference signal is provided separately, in addition to the aforementioned construction of the manufacturing line (see FIGS. 3A and 3B). At the time of inspection as illustrated in FIG. 3B, the simulated signal is input to the PLC 81 of the controller 80, instead of the reference signal, to actuate the HMA application device 70. Thus, the discharge amount inspection can be performed while keeping the pressing-roll device 40 in its stopped state. This is described in detail below.

As illustrated in FIG. 3B, the simulated-signal outputting section 60 includes: a rotary encoder 61; and a motor 61M serving as a dedicated driving source for driving and rotating the encoder 61 via a timing belt 62. The encoder 61 is a rotary encoder having the same specifications as the reference encoder 45 of the pressing-roll device 40. Accordingly, when the encoder 61 of the simulated-signal outputting section 60 is driven and rotated by the motor 61M, a signal having the same specifications as the reference signal of the reference encoder 45 of the pressing-roll device 40 is output from the simulated-signal outputting section 60.

Moreover, an inspection program for inspecting the discharge amount is installed in advance on the PLC 81. Furthermore, a control panel (not illustrated) of the manufacturing line is provided with an inspection button for starting the inspection program, and an input switch for inputting a provisional conveyance speed (m/min) in order to rotate the encoder 61 of the simulated-signal outputting section 60. When the inspection program is started by, for example, pressing the inspection button, the PLC 81 transmits a command value indicating the rotation speed (rpm) for inspection use to the amplifier 61A (FIG. 5) of the motor 61M of the simulated-signal outputting section 60. Thus, the simulated-signal outputting section 60 outputs a simulated signal.

Note here that the command value of the inspection-use rotation speed (rpm) is calculated by dividing the aforementioned provisional conveyance speed V1 (m/min) by the perimeter of the pressing roll 41. This calculation is performed, for example, by the PLC 81 every time a value of the provisional conveyance speed V1 is input from the input switch on the control panel, and the calculated rotation speed (rpm) is transmitted to the amplifier 61A of the motor 61M every time the calculation is made. Thus, the inspection operator can inspect the discharge amount by arbitrarily setting the provisional conveyance speed V1.

According to the construction including this simulated-signal outputting section 60, the discharge amount is inspected as follows.

First, as in FIG. 3B, the inspection operator operates a stop switch on the control panel to stop the manufacturing line which is up and running for manufacture as in FIG. 3A. When receiving the stop signal from the stop switch, the PLC 81 of the controller 80 sets a rotation-speed command value to zero; the rotation-speed command value will be transmitted to the amplifier 41A of the motor 41M of the pressing-roll device 40. Then, a drive current of zero amperage is ultimately output as the drive signal from the amplifier 41A to the motor 41M. That is, no drive signal is output, and thus, the rotation of the pressing rolls 41 is stopped.

Likewise, by receiving the stop signal, the PLC 81 of the controller 80 sets another rotation-speed command value to zero; the rotation-speed command value will be transmitted to the amplifier 22A of the motor 22M of the conveyance roller 22. Then, a drive current of zero amperage is ultimately output from the amplifier 22A to the motor 22M as the drive signal. That is, no drive signal is output, and thus, the rotation of the conveyance rollers 22 is stopped.

Then, the inspection operator inputs a provisional conveyance speed V1 from the control panel of the manufacturing line and presses the inspection button. The PLC 81 then outputs, to the amplifier 61A of the motor 61M of the simulated-signal outputting section 60, the rotation speed (rpm) corresponding to the provisional conveyance speed V1 (m/min), and drives the motor 61M.

In this way, the simulated-signal outputting section 60 outputs a simulated signal corresponding to the provisional conveyance speed V1 (m/min), and the simulated signal is input to the PLC 81, as illustrated in FIG. 3B. The simulated signal is used as the reference signal; the PLC 81 then generates valve open signals and valve close signals and transmits the valve open/close signals to the solenoid valve 75. Also, the simulated signal is used as the reference signal; the PLC 81 generates the rotation-speed command value for the gear pump 78 and transmits the command value to the amplifier 78A of the gear pump 78. Thus, the HMA application device 70 performs the same discharge operation as that performed during manufacture; in other words, it is brought into a state where it simulates the discharge operation performed at the time of manufacture.

Thereafter, the inspection operator samples the adhesive 7 discharged from the head 71 for a predetermined period of time in accordance with the aforementioned sampling procedure. Thus, it is possible to inspect the discharge amount by comparing the amount of the sampled adhesive 7 with the target value.

During the sampling operation, the rotation of the pressing rolls 41 and the conveyance rollers 22 is in a stopped state. In other words, the PLC 81 does not transmit a rotation-speed command value or transmits a command value of zero, to the respective amplifiers 41A and 22A of the pressing-roll device 40 and the conveyance rollers 22. Thus, the inspection operator can safely perform the operation of sampling the adhesive 7 discharged from the head 71.

It should be noted that, in this example, the rotation of the conveyance rollers 22 is also stopped, but the conveyance rollers 22 do not necessarily have to be stopped, because reasonable safety can be ensured if at least the rotation of the pressing rolls 41 is stopped. It goes without saying, however, that the safety of the inspection operation is improved remarkably if the conveyance rollers 22 are also stopped.

Figure 6:
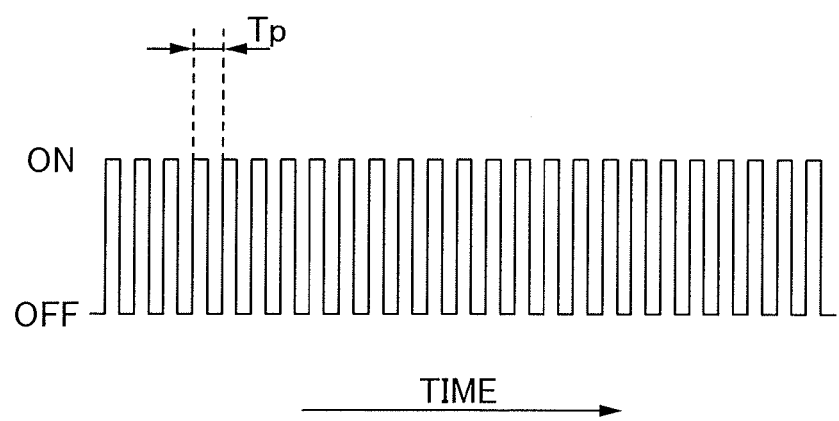
FIG. 6 is an explanatory diagram of a first modified example of a simulated-signal outputting section 60.

FIG. 6 is an explanatory diagram of a first modified example of the simulated-signal outputting section 60. In the foregoing first embodiment, a rotary encoder that outputs digital values is used as the simulated-signal outputting section 60. This first modified example is different therefrom in that a pulse generator is used. Otherwise, the first modified example is substantially the same as the foregoing first embodiment, so only the differences will be explained hereinbelow.

The pulse generator repeatedly generates rectangular pulses at a predetermined cycle Tp (sec.), as illustrated for example in FIG. 6. On the PLC 81, a counter circuit is installed in the form of a program; the counter circuit constitutes the simulated-signal outputting section in cooperation with the pulse generator. The counter circuit counts the number of pulses which are input from the pulse generator. The count value, whose initial value is zero, is reset to zero when the count value reaches 8192, which show a unit conveyance amount.

Further, the pulse generator is constructed in a manner such that the pulse generation cycle Tp can be changed depending on the input value of the provisional conveyance speed V1. More specifically, if the PLC 81 calculates the generation cycle Tp corresponding to the provisional conveyance speed V1 (m/min) in accordance with Equation (2) below, the pulse generator will generate pulses at the calculated generation cycle Tp. Thus, at the time of discharge amount inspection, the HMA application device 70 can operate by using the count values of the counter circuit as the simulated signal of the reference signal, and can thus replicate the discharge operation performed at the time of manufacture.

$$Tp=1/[(V1/\text{Product pitch } P \times 8192)/60] \qquad (2)$$

Figure 7:
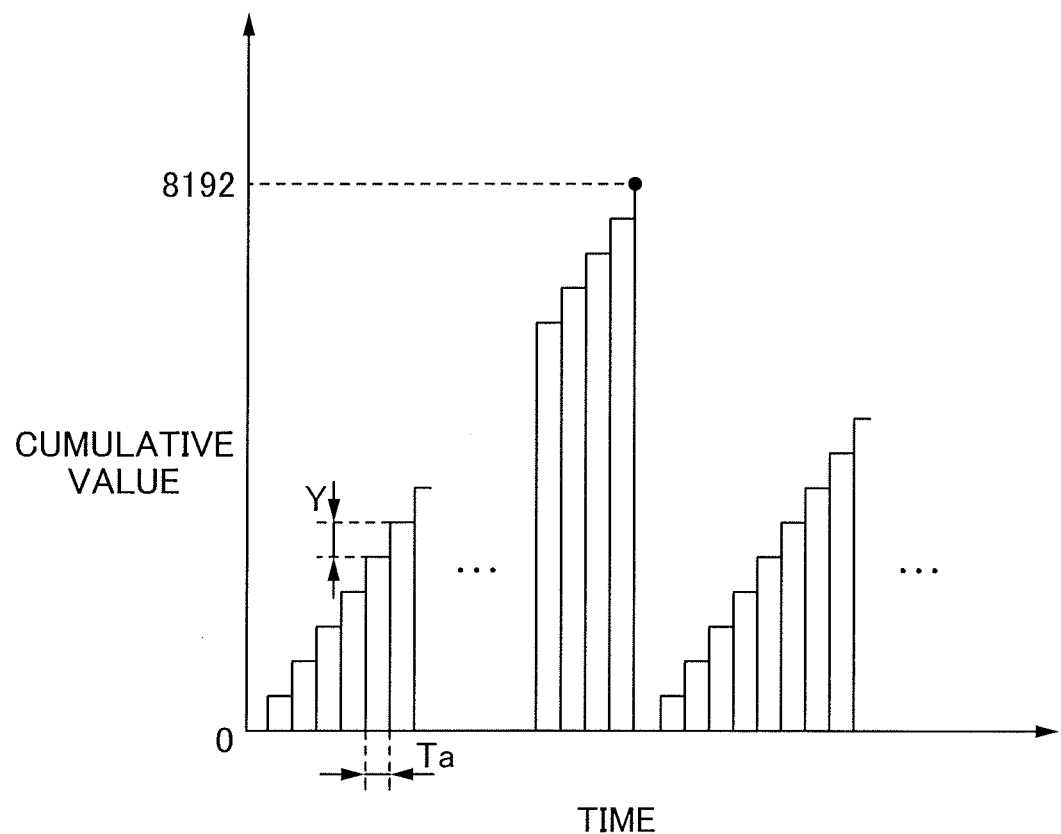
FIG. 7 is an explanatory diagram of a second modified example of a simulated-signal outputting section 60.

FIG. 7 is an explanatory diagram of a second modified example of the simulated-signal outputting section 60. In the foregoing first embodiment, the simulated-signal outputting section 60 is provided as an external device of the PLC 81 in the form of a rotary encoder. This second modified example is different therefrom in that the simulated-signal outputting section 60 is constructed as a program installed on the PLC 81. Otherwise, the second modified example is substantially the same as the foregoing first embodiment, so only the differences will be explained hereinbelow.

The PLC 81 includes an adding circuit in the form of a program. This adding circuit functions as the simulated-signal outputting section 60. More specifically, as illustrated in FIG. 7, the adding circuit performs a computation in which a predetermined incremental value Y is added up at a predetermined cycle Ta (sec.) and the sum is returned to zero at the same time that the cumulative value of this addition becomes greater than or equal to 8192, and the adding circuit repeat its endlessly. In this way, the adding circuit outputs discrete values, which range from 0 to 8191 and gradually increase with the passage of time.

The predetermined cycle Ta is, for example, the same value as the aforementioned control cycle Tc. The incremental value Y can be found from Equation (3) below. It should be noted that the "provisional conveyance speed V1" in Equation (3) is input by the inspection operator through the control panel of the manufacturing line.

$$Y=8192 \times V1/(\text{Product pitch } P)/(1/Ta \times 60) \qquad (3)$$

Thus, by using this incremental value Y, the reference signal, which is to be output at the time of conveyance of the first sheet 1a at the conveyance speed V1, is simulated.

—Second Embodiment—

Figure 8A:
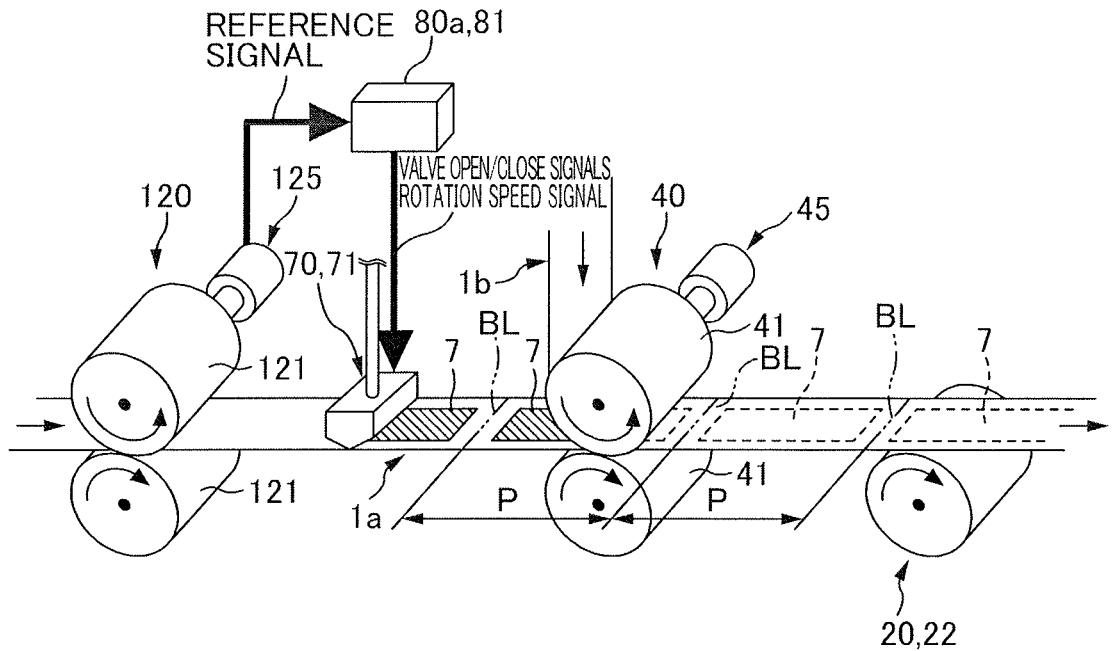
FIGS. 8A and 8B are explanatory diagrams of a manufacturing line according to a second embodiment.
Figure 8B:
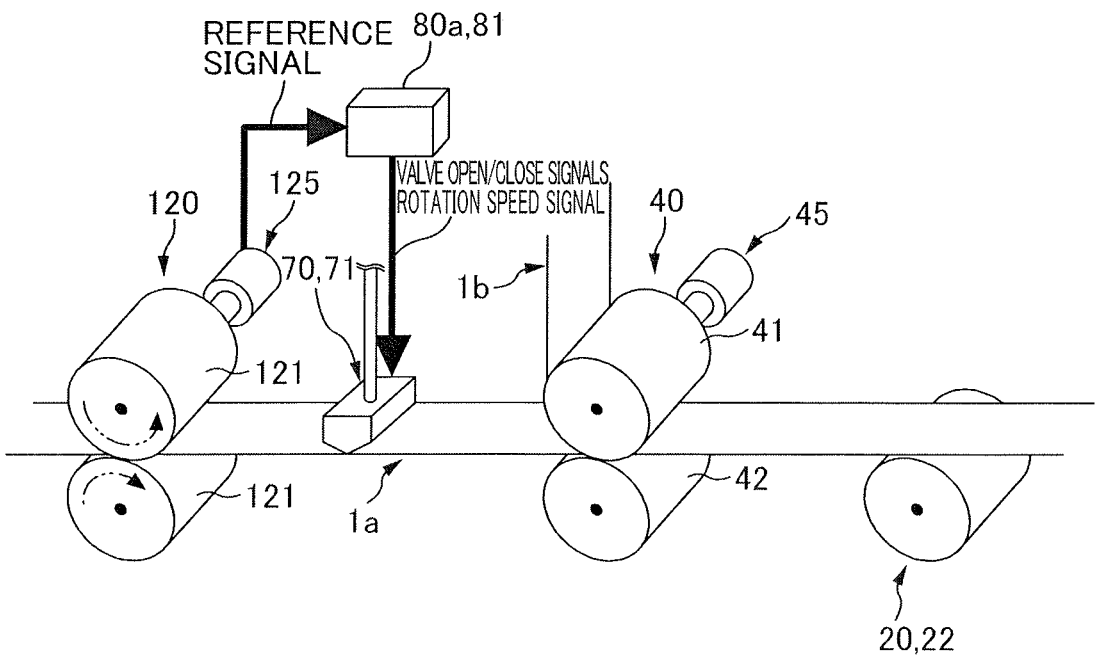

FIGS. 8A and 8B are explanatory diagrams of a manufacturing line according to a second embodiment. FIG. 8A illustrates a state at the time of manufacture of the diapers 1, and FIG. 8B illustrates a state at the time of inspection of the discharge amount of the HMA application device 70.

In the foregoing first embodiment, the pressing-roll device 40 is given as an example of the processing device. This second embodiment is different therefrom in that it includes a second processing device 120 in addition to the pressing-roll device 40. And also, This second embodiment is different in that the encoder 125 of the second processing device 120 functions as the reference encoder outputting the reference signal and thus the digital-value signal of the encoder 45 of the pressing-roll device 40 is not used as the reference signal. Moreover, the construction of the second embodiment is different in that it does not include the simulated-signal outputting section 60 of FIG. 3B, and that the encoder 125 outputs the reference signal instead of the simulated signal at the time of inspection. In other words, the encoder 135 corresponds to both the "first-reference-signal outputting section" and the "second-reference-signal outputting section" as recited in the claims.

Otherwise, this embodiment is substantially the same as the foregoing first embodiment, so only the differences will be explained hereinbelow. Note that hereinbelow, the pressing-roll device 40 as described in the first embodiment is referred to as the first pressing-roll device 40 or the first processing device 40.

As illustrated in FIG. 8A, the second processing device 120 is arranged, for example, at a position so that the head 71 of the HMA application device 70 is located in the MD direction between the device 120 and the first processing device 40. In this example, the second processing device 120 (also referred to hereinafter as the second pressing-roll device 120) is also a pressing-roll device having substantially the same construction as the first processing device 40.

Figure 9:
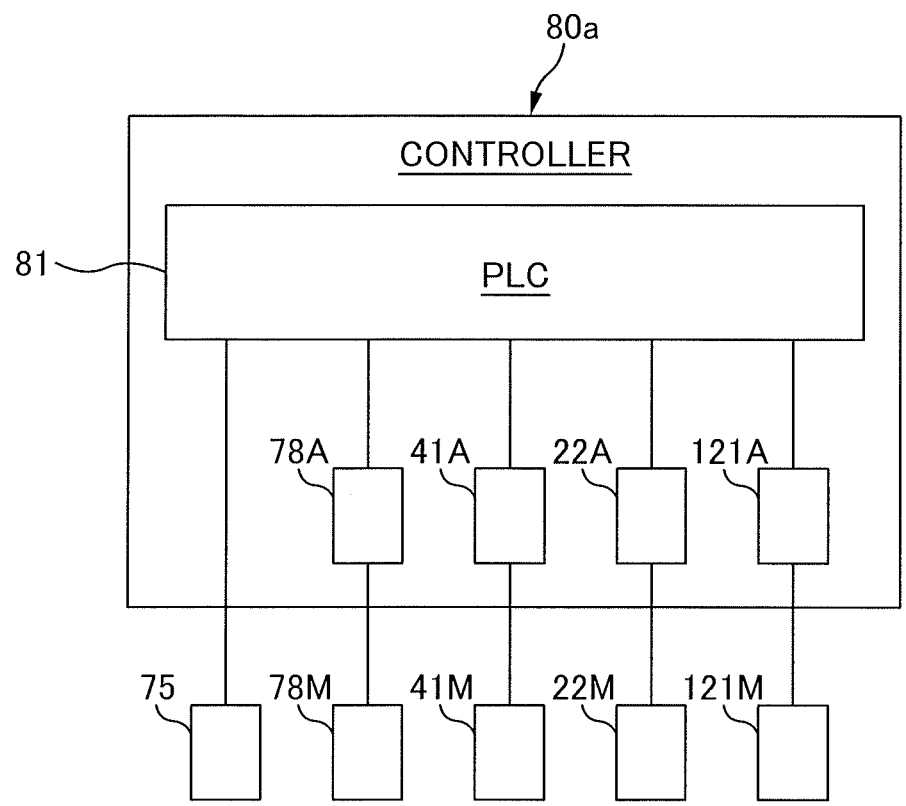
FIG. 9 is a schematic configuration diagram of a controller 80a according to the second embodiment.

More specifically, also the second processing device 120 includes a pair of upper and lower pressing rolls 121 and 121 which are driven and rotated by a motor 121M (not illustrated in FIG. 8A; see FIG. 9) serving as a driving source. On the shaft end of one of the pressing rolls 121, an encoder 125 is provided. Moreover, as illustrated in FIG. 9, a controller 80a includes an amplifier 121A for the motor 121M of the second processing device 120. At the time of manufacture of the diapers 1, the PLC 81 of the controller 80a outputs to the amplifier 121A a command value indicating the rotation speed (rpm) of the pressing rolls 121. The amplifier 121A outputs a drive signal, on the basis of this rotation-speed command value, to the motor 121M in a manner so as to reduce the deviation between the command value and the actual value of the rotation speed. Note that also in the second processing device 120, the aforementioned drive signal is a drive current; that is, the motor 121M is driven by employing the drive current as its motive force. It goes without saying that the actual value of the rotation speed is measured by the encoder 125 and transmitted to the amplifier 121A.

As described above, in this second embodiment, the encoder 125 of the second processing device 120 functions as the reference encoder, instead of the encoder 45 of the first processing device 40. In other words, the encoder 125 of the second processing device 120 outputs the reference signal (corresponding to "first reference signal"). Thus, at the time of manufacture of the diapers 1, the reference signal is input from the encoder 125 to the PLC 81, and the PLC 81 controls the discharge operation of the HMA application device 70.

Moreover, at the time of manufacture of the diapers 1, the command value of the rotation speed (rpm) of the first processing device 40 is calculated by employing, as the command value, the conveyance speed V1 calculated on the basis of the reference signal of the reference encoder 125 and the aforementioned Equation (1). More specifically, the aforementioned command value of the rotation speed is calculated by dividing the calculated conveyance speed V1 by the perimeter (m) of the roll 41 of the first processing device 40. In this way, the drive signal for the first processing device 40, which is ultimately output from the amplifier 41A, is generated by the controller 80a on the basis of the reference signal.

In the manufacturing line of the second embodiment, the inspection of the discharge amount of the HMA application device 70 is performed in a state where the second pressing-roll device 120 is in operation while the first pressing-roll device 40 is stopped. Thus, safety is ensured at least against the first pressing-roll device 40. The procedure etc. therefor will be described in detail below.

First, as in FIG. 8B, an inspection operator operates a stop switch on the control panel to stop the manufacturing line which is up and running for manufacture, as in FIG. 8A. When receiving the stop signal from the stop switch, the PLC 81 of the controller 80a sets the rotation-speed command values to zero; the rotation-speed command values will be transmitted to the amplifiers 41A and 121A of the first pressing-roll device 40 and the second pressing-roll device 120. Then, drive currents of zero amperage are ultimately output as the drive signals from the amplifiers 41A and 121A to the corresponding motors 41M and 121M. That is, no drive signal is output, and thus, the rotation of the pressing rolls 41 and the pressing rolls 121 is stopped.

Likewise, by receiving the stop signal, the PLC 81 of the controller 80a sets another rotation-speed command value to zero; the rotation-speed command value will be transmitted to the amplifier 22A of the motor 22M of the conveyance rollers 22. Then, a drive current of zero amperage is ultimately output from the amplifier 22A to the motor 22M as the drive signal. That is, no drive signal is output, and thus, the rotation of the conveyance rollers 22 is stopped.

Then, the inspection operator inputs a provisional conveyance speed V1 from the control panel of the manufacturing line and presses the inspection button. The PLC 81 then outputs, to the amplifier 121A (FIG. 9) of the motor 121M of the second pressing-roll device 120, the rotation speed (rpm) corresponding to the provisional conveyance speed V1 (m/min), and drives the motor 121M.

In this way, the pressing rolls 121 of the second pressing-roll device 120 are driven and rotated at the provisional conveyance speed V1, as illustrated by the long dashed double-dotted arrows in FIG. 8B. Thus, the reference encoder 125 of the second pressing-roll device 120 outputs a reference signal (corresponding to "second reference signal") corresponding to the provisional conveyance speed V1, and the reference signal is input to the PLC 81. Using this reference signal, the PLC 81 then generates valve open signals and valve close signals and transmits the valve open/close signals to the solenoid valve 75. Also, using this reference signal, the PLC 81 generates the rotation-speed command value for the gear pump 78 and transmits the command value to the amplifier 78A (FIG. 9) of the gear pump 78. Thus, the HMA application device 70 performs the same discharge operation as that performed during manufacture; in other words, it is brought into a state where it simulates the discharge operation performed at the time of manufacture.

Thereafter, the inspection operator samples the adhesive 7 discharged from the head 71 for a predetermined period of time in accordance with the aforementioned sampling procedure. Thus, it is possible to inspect the discharge amount by comparing the amount of the sampled adhesive 7 with the target value.

During the inspection, the second pressing-roll device 120 is in operation, while the first pressing-roll device 40 and the rotation of the conveyance rollers 22 are in a stopped state. In other words, the PLC 81 does not transmit a rotation-speed command value or transmits a command value of zero, to the respective amplifiers 41A and 22A of the pressing-roll device 40 and the conveyance rollers 22. Thus, the safety of the inspection operator is ensured, at least against the second pressing-roll device 120 and the conveyance rollers 22.

At the time of driving and rotating the second pressing-roll device 120 during the inspection of FIG. 8B, it is preferable to form a space between the pressing rolls 121 and 121 and release the pressing force therebetween. That is, it is preferable to make the pressing rolls 121 and 121 idle. In this way, it is possible to reliably prevent the first sheet 1a from being conveyed unnecessarily by the driving rotation of the pressing rolls 121.

An example of such a mechanism for releasing the pressing force may be a construction including: a guiding mechanism (not illustrated) for guiding at least one of the pair of upper and lower pressing rolls 121 and 121 such that the roll 121 can move relatively in the vertical direction with respect to the other roll 121; and an actuator (not illustrated), such as a hydraulic cylinder, that supports the one roll 121 so as to be movable in the vertical direction. The activation of the actuator is triggered by a signal issued upon pressing the aforementioned inspection button. Thus, a space is formed between the pressing rolls 121 and 121, and the pressing rolls 121 and 121 are brought out of contact from one another, at least before starting to drive and rotate the pressing rolls 121.

—Third Embodiment—

Figure 10A:
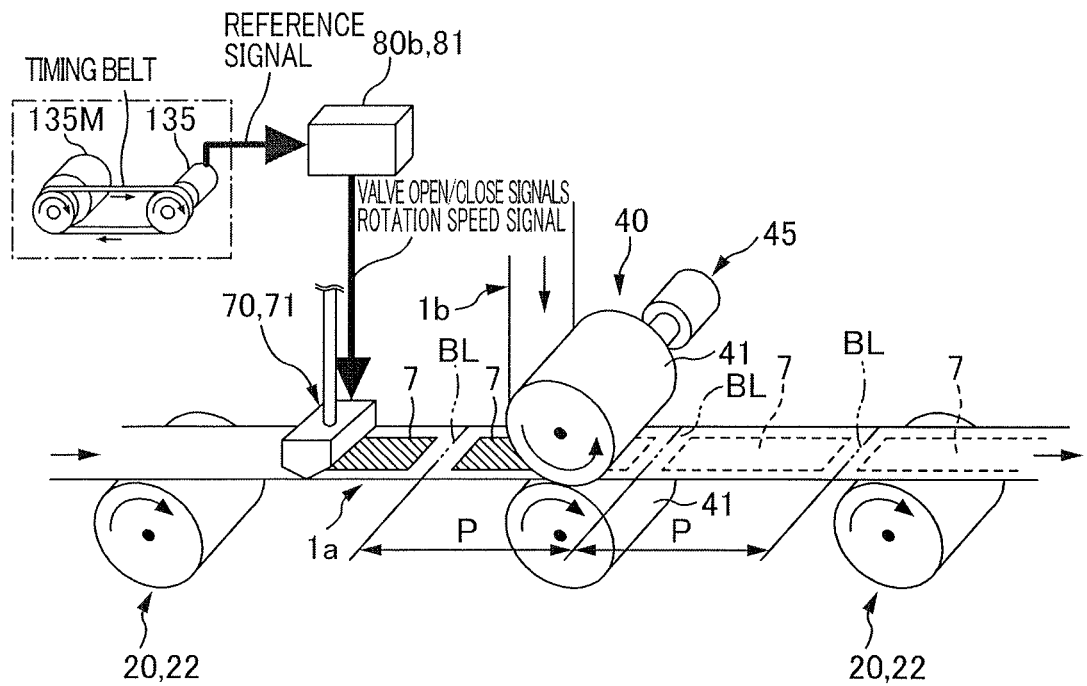
FIGS. 10A and 10B are explanatory diagrams of a manufacturing line according to a third embodiment.
Figure 10B:
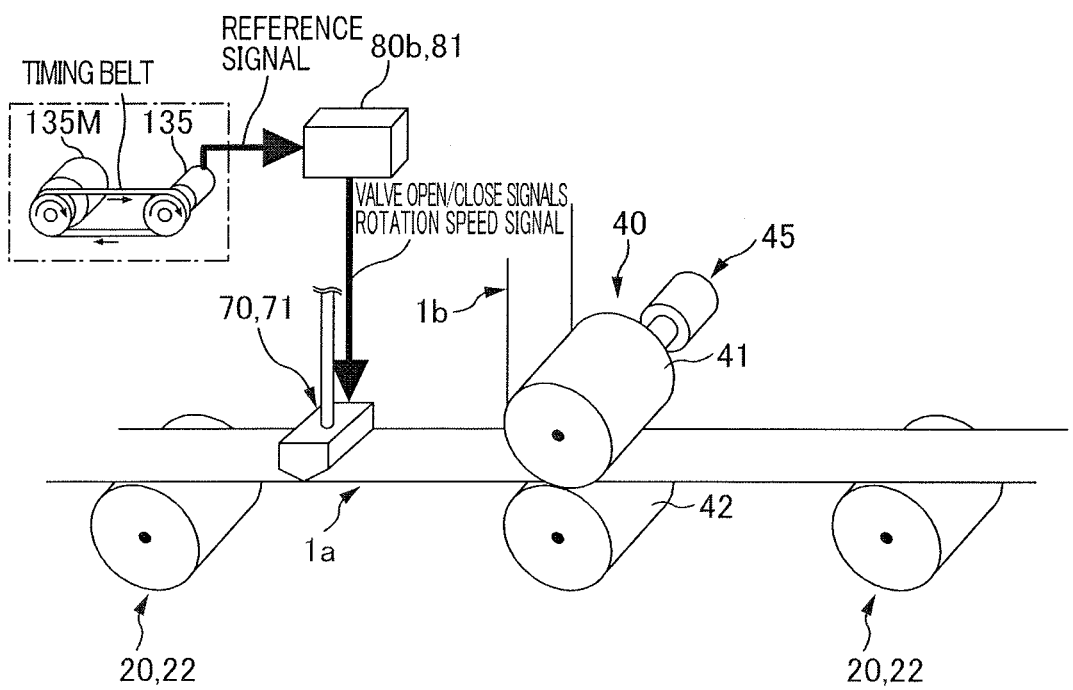

FIGS. 10A and 10B are explanatory diagrams of a manufacturing line according to a third embodiment. FIG. 10A illustrates a state at the time of manufacture of the diapers 1, and FIG. 10B illustrates a state at the time of inspection of the discharge amount of the HMA application device 70.

In the foregoing first embodiment, the reference encoder 45 that outputs the reference signal is provided as an attachment to the processing device 40, and the reference encoder 45 outputs the reference signal as a result of the processing device 40 being driven. Regarding this point, the third embodiment of FIG. 10B differs therefrom in that it includes a rotary encoder 135 which is driven independently by a driving source separate from the driving system of the processing device 40 and in that the encoder 135 outputs the reference signal (corresponding to "first reference signal").

Owing to these differences, the third embodiment can make the HMA application device 70 operate on the basis of the reference signal (corresponding to "second reference signal") of the encoder 135 at the time of inspection of the discharge amount, even when the processing device 40 is in its stopped state. In other words, the encoder 135 corresponds to both the "first-reference-signal outputting section" and the "second-reference-signal outputting section" as recited in the claims. Otherwise, this embodiment is substantially the same as the foregoing first embodiment, so only the differences will be explained hereinbelow.

Figure 11:
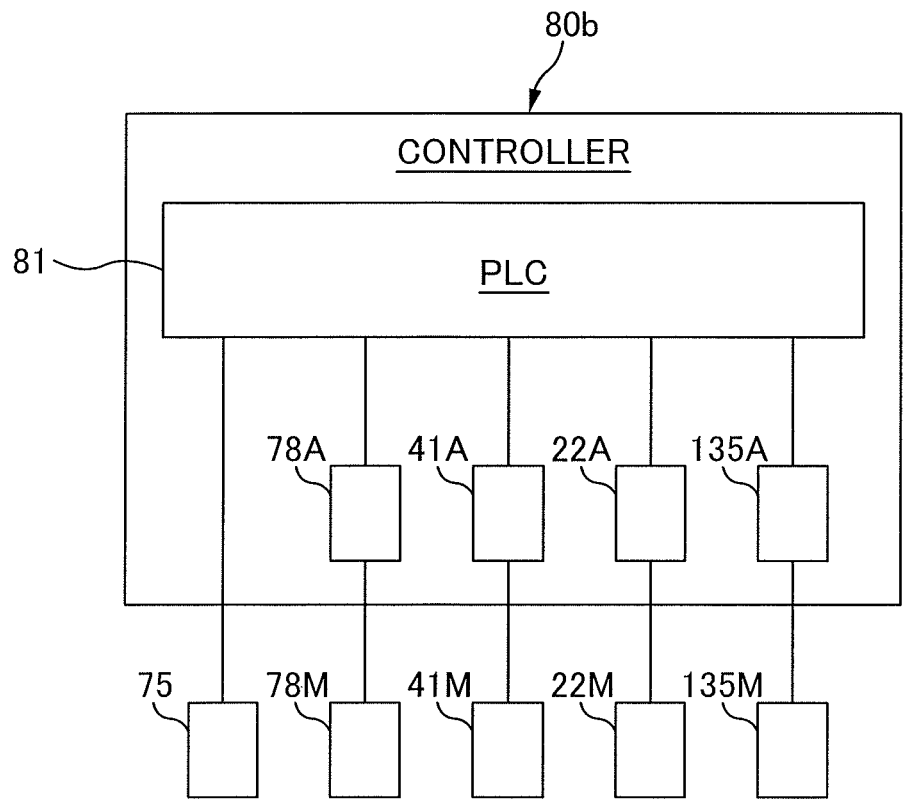
FIG. 11 is a schematic configuration diagram of a controller 80b according to the third embodiment.

As illustrated in FIGS. 10A and 11, the motor 135M serving as the driving source of the encoder 135 that outputs the reference signal is dedicated to the encoder 135 and separate from the motor 41M of the processing device 40. A controller 80b illustrated in FIG. 11 also includes an amplifier 135A for the motor 135M of the encoder 135. Hereinbelow, this encoder 135 is referred to as a "reference encoder", and the encoder 45 of the pressing-roll device 40, which is the processing device 40, is referred to simply as an "encoder", and not the "reference encoder".

At the time of manufacture of the diapers 1, a command value of a rotation speed corresponding to the conveyance speed V1 of the first sheet 1a is input from the PLC 81 to the amplifier 135A of the reference encoder 135, and the motor 135M of the reference encoder 135 is driven on the basis of this command value.

Moreover, the pressing-roll device 40, which serves as the processing device 40, and the conveyance rollers 22 are driven in synchronization (in cooperation) with the reference signal that is output from the reference encoder 135. More specifically, based on the aforementioned Equation (1), the PLC 81 calculates the conveyance speed V1 from the time interval ΔT at which the digital values in the reference signal are output. Then, the PLC finds the command value of the rotation speed by dividing the calculated conveyance speed V1 by the perimeter of the pressing roll 41, and transmits this command value to the amplifier 41A of the motor 41M that drives the pressing rolls 41.

Likewise, the PLC finds the command value of the rotation speed by dividing the aforementioned conveyance speed V1 by the perimeter of the conveyance roller 22, and transmits this command value to the amplifier 22A of the motor 22M that drives the conveyance rollers 22. Thus, the peripheral speed (m/min) of each pressing roll 41 is controlled so as to be substantially the same as the peripheral speed (m/min) of each conveyance roller 22. As a result, the pressing rolls 41 are rotated in synchronization (in cooperation) with the conveyance operation of the first sheet 1a.

It goes without saying that, at the time of manufacture, the HMA application device 70 is also controlled by the PLC 81 on the basis of the aforementioned reference signal and thereby the adhesive 7 is discharged from the head 71, as illustrated in FIG. 10A.

On the contrary, as in FIG. 10B, at the time of inspection of the discharge amount, an inspection operator operates a stop switch on the control panel of the manufacturing line to stop the manufacturing line which is up and running for manufacture, as in FIG. 10A. When receiving the stop signal from the stop switch, the PLC 81 of the controller 80b sets the rotation-speed command value of the motor 135M of the reference encoder 135 to zero, and outputs the command value to the amplifier 135A. Then, a drive current of zero amperage is ultimately output as the drive signal from the amplifier 135A of the reference encoder 135 to the motor 135M thereof. That is, no drive signal is output, and thus, the rotation of the reference encoder 135 is stopped and the outputting of the reference signal is stopped.

On the other hand, because no reference signal is output, the rotation-speed command values to be transmitted from the PLC 81 to the amplifier 41A of the pressing-roll device 40 and to the amplifier 22A of the conveyance rollers 22 become zero automatically. Thus, drive currents of zero amperage are ultimately output as the drive signals from the respective amplifiers 41A and 22A to the corresponding motors 41M and 22M. That is, no drive signal is output, and thus, the rotation of the pressing rolls 41 and the conveyance rollers 22 is stopped.

Then, the inspection operator inputs a provisional conveyance speed V1 from the control panel of the manufacturing line and presses the inspection button. Then, in accordance with the inspection program, the PLC 81 outputs, to the amplifier 135A of the motor 135M of the reference encoder 135, the rotation speed (rpm) corresponding to the provisional conveyance speed V1 (m/min), and drives the motor 135M. In this way, the reference encoder 135 outputs a reference signal corresponding to the provisional conveyance speed V1 (m/min), and this reference signal is input to the PLC 81, as illustrated in FIG. 10B. Using this reference signal, the PLC 81 then generates valve open signals and valve close signals and transmits the valve open/close signals to the solenoid valve 75. Also, using this reference signal, the PLC 81 generates the rotation-speed command value for the gear pump 78 and transmits the command value to the amplifier 78A of the gear pump 78. Thus, the HMA application device 70 performs the same discharge operation as that performed during manufacture; in other words is brought into a state where it simulates the discharge operation performed at the time of manufacture.

Moreover, the inspection program is designed in advance such that, during the operation of the inspection program, the PLC 81 never transmits a rotation-speed command value, or always transmits a command value of zero, to both the amplifier 41A of the pressing-roll device 40 and the amplifier 22A of the conveyance rollers 22. Thus, no drive signal is output from the respective amplifiers 41A and 22A to the corresponding motors 41M and 22M, and the pressing rolls 41 and the conveyance rollers 22 are therefore kept in a stopped state. Thus, the inspection operator can safely perform the operation of sampling the adhesive 7 discharged from the head 71.

—Other Embodiments—

Although embodiments of the present invention have been described above, the invention is not limited to the foregoing embodiments, and modifications, such as those described below, are possible.

In the foregoing embodiments, a hot-melt adhesive 7 is described as an example of the "adhesive". The adhesive, however, is not limited thereto and other types of adhesives are usable, as far as it is an adhesive that is discharged toward the first sheet 1a, which is an example of a workpiece.

In the foregoing embodiments, the adhesive 7 is discharged intermittently in order to apply the adhesive 7 toward each target application region on the first sheet 1a for every unit conveyance amount of the first sheet 1a. This, however, is not a limitation. For example, the adhesive 7 may be emitted continuously toward the first sheet 1a, regardless of the unit conveyance amount of the first sheet 1a.

In the foregoing embodiments, a disposable diaper 1 that is worn by a subject and absorbs excreted fluid thereof is described as an example of the absorbent article. The absorbent article, however, is not limited thereto as far as it absorbs excreted fluid such as urine or menstrual blood, and examples may include sanitary napkins and sheets for pets that absorb excreted fluid of pets.

In the foregoing embodiments, the pressing-roll devices 40 and 120 are described as examples of processing devices in explaining the generalized construction of the manufacturing line. The processing device, however, is not limited thereto, as far as it is a device that performs processing related to the manufacture of the absorbent article. For example, the processing device may be an embossing-roll device that performs embossing, the die cutter device 90, the fiber-depositing device 30, or any other device. That is, in addition to the process of placing another semi-finished product 1b on the semi-finished product 1a which is the workpiece and pressing the semi-finished products together, the concept of processing includes: a process of deforming the semi-finished product 1a by means such as applying an external force to the semi-finished product 1a; a process of separating the semi-finished product 1a on a product-by-product basis; a process of placing another component on the semi-finished product 1a, and the like.

In the foregoing embodiments, the first sheet 1a in the form of a continuous sheet is described as an example of the workpiece. The workpiece, however, does not have to be in the form of a continuous sheet. For example, workpieces separated individually on a product-by-product basis may be conveyed at predetermined pitches in the conveying direction.

In the foregoing embodiments, an encoder that outputs a digital value at every predetermined rotation angle is described as an example of the rotary encoder. The rotary encoder, however, is not limited thereto. For example, it is possible to use an encoder that generates a pulse at every predetermined rotation angle and that outputs a reset signal every time it reaches a rotation angle corresponding to the product pitch P (e.g., one revolution). In this case, the PLC 81 counts the number of pulses output from the encoder and resets the count value to zero every time the PLC 81 receives a reset signal, and thereby this encoder cooperates with the PLC 81 and functions similarly to the encoder of the foregoing embodiments.

In the foregoing embodiments, a non-contacting discharge opening is described in which the nozzle N which serves as the discharge opening is not in contact with the first sheet 1*a* at the tip thereof. In other words, the tip of the nozzle N is arranged with a space between it and the first sheet 1*a*. This, however, is not a limitation, and a contact discharge opening may be used. That is, the tip of the nozzle N or a member disposed on the tip may be in contact with the first sheet 1*a*. As an example of the contact discharge opening, the following construction can be provided: the tip of the nozzle N is provided with a rotating spherical element such as the ball of a ballpoint pen, the spherical element is moved by keeping in contact with the first sheet 1*a*.

In the foregoing embodiments, only one HMA application device 70 is described as an example in explaining the generalized construction of the manufacturing line (e.g., FIG. 3A). However, the number of HMA application devices 70, 70, . . . may be plural, as illustrated in FIG. 1. That is, the application devices may be arranged at a plurality of positions along the MD direction. In this case, as a matter of course, the specifications (the shape, number, and position of the nozzle (s) N of the head 71, the supply rate of the pump 78, etc.) of the respective HMA application devices 70, 70, . . . are determined depending on how each HMA application device 70 should cause the semi-finished products 1*a* and 1*a* to adhere to each other, and in some cases the specifications differs from one another. It also goes without saying that, in association therewith, the first and second setting values related to the valve open/close signals may differ for each HMA application device 70. At the time of inspection of the adhesive discharge amount in the first embodiment, the controller 80 generates valve open/close signals etc. in correspondence with the respective adhesive discharging devices 70, 70, . . . on the basis of the simulated signal output from the simulated-signal outputting section 60; therefore, the controller 80 outputs the respective valve open/close signals etc. that have been generated to the corresponding HMA application devices 70. Further, at the time of the same inspection in the second embodiment, the controller 80*a* generates valve open/close signals etc. in correspondence with the respective adhesive discharging devices 70, 70, . . . on the basis of the reference signal output from the reference encoder 125; therefore, the controller 80*a* outputs the respective valve open/close signals etc. that have been generated to the corresponding HMA application devices 70. Moreover, at the time of the same inspection in the third embodiment, the controller 80*b* generates valve open/close signals etc. in correspondence with the respective adhesive discharging devices 70, 70, . . . on the basis of the reference signal output from the reference encoder 135; therefore, the controller 80*b* outputs the respective valve open/close signals etc. that have been generated to the corresponding HMA application devices 70.

In the foregoing embodiments, a drive current was described as an example of the drive signal. The drive signal, however, may be a voltage, or any other signal.

In the first and second embodiments, the amplifier 22A performs speed control, but instead, it may perform positional control. This is described in detail. The PLC 81 converts the reference signal into a signal indicating rotational position and inputs this signal to the amplifier 22A. Then, by employing this rotational position as a command value, the amplifier 22A finds the deviation between this command value and the actual value of the rotational position transmitted from the encoder of the conveyance roller 22, and calculates the command value of the rotation speed on the basis of this deviation. The amplifier may then calculate the drive current on the basis of the deviation between the command value of the rotation speed and the actual value of the rotation speed transmitted from the encoder, and output the drive current to the motor 22M as the drive signal.

The inspection program is designed in advance such that while the inspection program is in operation, that is, in a state where the inspection button has been pressed, the PLC 81 constantly outputs a predetermined fixed value to the amplifier 22A of the conveyance rollers 22, the fixed value serving as the command value of the rotational position. Thus, no drive signal is output from the amplifier 22A to the motor 22M, and the conveyance rollers 22 are therefore kept in their stopped state. Thus, the inspection operator can safely perform the operation of sampling the adhesive 7 discharged from the head 71.

In the third embodiment, the amplifiers 41A and 22A perform speed control, but instead, they may perform positional control. This is described in detail. The PLC 81 converts the reference signal into a signal indicating rotational position and inputs this signal to the amplifiers 41A and 22A. Then, by employing this rotational position as a command value, each amplifier 41A, 22A finds the deviation between this command value and the actual value of the rotational position transmitted from the encoder, and calculates the command value of the rotation speed on the basis of this deviation. Each amplifier may then calculate the drive current on the basis of the deviation between the command value of the rotation speed and the actual value of the rotation speed transmitted from the encoder, and output the drive current to the corresponding motor 41M, 22M as the drive signal.

The inspection program is designed in advance such that while the inspection program is in operation, that is in a state where the inspection button has been pressed, the PLC 81 constantly outputs a predetermined fixed value to both the amplifier 41A of the pressing-roll device 40 and the amplifier 22A of the conveyance rollers 22, the fixed value serving as the command value of the rotational position. Thus, no drive signal is output from the amplifiers 41A and 22A to the corresponding motors 41M and 22M, and the pressing rolls 41 and the conveyance rollers 22 are therefore kept in their stopped state.

REFERENCE SIGNS LIST

1: disposable diaper (absorbent article);
1*a*: first sheet (semi-finished product, workpiece);
1*b*: second sheet (semi-finished product);
2: top sheet; 2*a*: top sheet; 2*b*: top sheet; 2*c*: top sheet;
2*r*: top sheet roll;
3: absorber; 3*a*: pulp fiber;
4: back sheet; 4*r*: back sheet roll;
6: carrier sheet; 6*r*: carrier sheet roll;
7: hot-melt adhesive (adhesive);
8: gather sheet; 8*a*: three-dimensional gather sheet;
8*g*: three-dimensional gathers; 8*r*: gather sheet roll;
9: elastic member; 20: conveyance mechanism; 21: belt conveyor;
22: conveyance roller; 22A: amplifier; 22M: motor;
28: reels; 30: fiber-stacking device;
40: pressing-roll device (processing device, first processing device);
41: press rolls; 41*a*: amplifier; 41*m*: motor (driving source);
45: reference encoder (first-reference-signal outputting section, first rotary encoder);

60: simulated-signal outputting section (second-reference-signal outputting section);
61: rotary encoder (second rotary encoder); 61A: amplifier; 61M: motor (driving source);
62: timing belt;
70: HMA application device (adhesive discharging device);
70a: HMA application device (adhesive discharging device);
70b: HMA application device (adhesive discharging device);
70c: HMA application device (adhesive discharging device);
70d: HMA application device (adhesive discharging device);
71: head; 73: flow path; 74: valve; 75: solenoid valve; 77: tank;
78: gear pump; 78c: casing; 78a: amplifier; 78m: motor; 79: relief valve;
80: controller; 80a: controller; 80b: controller; 81: PLC;
90: Die cutter device; 91a: cutter roll; 91b: anvil roll;
95: slitter device; 97: elastic-member supplying device;
120: second pressing-roll device (second processing device);
121: press rolls; 121A: amplifier; 121M: motor;
125: reference encoder (first-reference-signal outputting section, second-reference-signal outputting section);
135: reference encoder (first-reference-signal outputting section, second-reference-signal outputting section);
135A: amplifier; 135M: motor;
N: nozzle; BL: boundary position

The invention claimed is:

1. An absorbent-article manufacturing apparatus for manufacturing an absorbent article by performing processing on and discharging an adhesive onto a workpiece related to the absorbent article while conveying the workpiece in a conveying direction, the absorbent-article manufacturing apparatus comprising:
   a first-reference-signal outputting section configured to output a first reference signal indicating a conveyance amount of the workpiece;
   a second-reference-signal outputting section configured to output a second reference signal indicating the conveyance amount of the workpiece;
   a processing device configured to perform processing on the workpiece on the basis of a drive signal;
   an adhesive discharging device configured to discharge the adhesive toward the workpiece on the basis of a discharge signal; and
   a controller configured to generate the drive signal and the discharge signal,
   wherein
   the second-reference-signal outputting section is configured to generate, as the second reference signal, a simulated signal of the first reference signal,
   at the time of manufacturing the absorbent article,
      the controller generates the drive signal on the basis of the first reference signal output from the first-reference-signal outputting section and outputs the drive signal to the processing device, and
      the controller also generates the discharge signal on the basis of the first reference signal and outputs the discharge signal to the adhesive discharging device, and
   at the time of inspecting a discharge amount of the adhesive discharged from the adhesive discharging device,
      the controller generates the discharge signal on the basis of the second reference signal output from the second-reference-signal outputting section and outputs the discharge signal to the adhesive discharging device,
      the controller does not output the drive signal to the processing device,
      the first reference signal from the first-reference-signal outputting section is stopped from being output,
      the simulated signal is input to the controller, and
      the controller generates the discharge signal on the basis of the simulated signal and outputs the discharge signal to the adhesive discharging device.

2. The absorbent-article manufacturing apparatus according to claim 1, wherein:
   the first-reference-signal outputting section includes a first rotary encoder;
   the second-reference-signal outputting section includes a second rotary encoder provided separately from the first rotary encoder;
   the second rotary encoder is configured to generate a rotation signal having the same specifications as the first reference signal by being driven and rotated by a driving source separate from a driving source of the first rotary encoder; and
   at the time of the inspecting the discharge amount of the adhesive discharged from the adhesive discharging device,
      the first reference signal from the first rotary encoder is stopped from being output, and
      the rotation signal of the second rotary encoder is input to the controller as the simulated signal.

3. The absorbent-article manufacturing apparatus according to claim 1, wherein:
   when the conveyance amount of the workpiece equivalent to a manufacturing pitch for manufacturing the absorbent article is defined as a unit conveyance amount, the first-reference-signal outputting section outputs, as the outputting of the first reference signal, a digital value having a magnitude proportional to the conveyance amount of the workpiece repeatedly for every unit conveyance amount;
   the controller includes a processor and a program executable by the processor;
   the controller has the second-reference-signal outputting section as the program; and
   the second-reference-signal outputting section is configured to find a cumulative value by repeatedly adding up a predetermined incremental value at a predetermined cycle, and output the cumulative value as the second reference signal.

4. The absorbent-article manufacturing apparatus according to claim 1, wherein:
   the adhesive discharging device includes
      a head that has at least one discharge opening,
      a pump that is configured to supply the adhesive to the discharge opening of the head, and
      a valve that is provided in correspondence with the discharge opening and that is configured to intermittently discharge adhesive from the discharge opening by performing an opening/closing operation; and
   the discharge signal includes
      a supply amount signal that defines a supply amount of the adhesive supplied from the pump to the head per unit time, and
      a valve open/close signal that defines the opening/closing operation of the valve.

5. The absorbent-article manufacturing apparatus according to claim 1, further comprising a conveyance mechanism configured to convey the workpiece in the conveying direction,
wherein:
   the conveyance mechanism is configured to be driven on the basis of the drive signal output from the controller;

at the time of manufacturing the absorbent article, the controller generates the drive signal and outputs the drive signal to the conveyance mechanism; and at the time of inspecting the discharge amount of the adhesive discharged from the adhesive discharging device, the controller stops outputting the drive signal to the conveyance mechanism.

6. The absorbent-article manufacturing apparatus according to claim 1, wherein:

a plurality of the adhesive discharging devices are arranged at respective positions along the conveying direction; and at the time of inspecting the discharge amount of the adhesive discharged from each adhesive discharging device, the controller generates, on the basis of the second reference signal output from the second-reference-signal outputting section, a plurality of the discharge signals in correspondence with the respective adhesive discharging devices, and the controller outputs each of the generated discharge signals to a corresponding one of the adhesive discharging devices.

* * * * *